US005609770A

United States Patent [19]
Zimmerman et al.

[11] Patent Number: 5,609,770
[45] Date of Patent: Mar. 11, 1997

[54] GRAPHICAL OPERATOR MACHINE INTERFACE AND METHOD FOR INFORMATION ENTRY AND SELECTION IN A DIALYSIS MACHINE

[75] Inventors: Eric Zimmerman, Littleton; Jim Rosa, Conifer; Steve Love, Bailey; Catherine DiMuzio, Denver, all of Colo.

[73] Assignee: COBE Laboratories, Inc., Lakewood, Colo.

[21] Appl. No.: 486,944

[22] Filed: Jun. 7, 1995

[51] Int. Cl.$^6$ .................. B01D 61/32; G06F 17/30; G06F 159/00
[52] U.S. Cl. .................. 210/739; 210/85; 210/143; 210/646; 395/326; 395/356; 604/5
[58] Field of Search .................. 210/85, 138, 143, 210/321.69, 636, 646, 739, 929, 96.2, 647; 604/4–6; 364/413.01, 413.02, 413.07; 395/140, 155, 160, 161, 924

[56] References Cited

U.S. PATENT DOCUMENTS

| | | | |
|---|---|---|---|
| 4,370,983 | 2/1983 | Lichtenstein | 210/929 |
| 4,756,706 | 7/1988 | Kerns et al. | 604/66 |
| 4,796,634 | 1/1989 | Huntsman et al. | 128/662.01 |
| 4,990,258 | 2/1991 | Bjare et al. | 210/647 |
| 5,276,611 | 1/1994 | Ghiraldi | 604/4 |
| 5,319,363 | 6/1994 | Welch et al. | 340/825.36 |
| 5,326,476 | 7/1994 | Grogan et al. | 210/646 |
| 5,472,614 | 12/1995 | Rossi | 210/143 |
| 5,486,286 | 1/1996 | Peterson et al. | 210/646 |

FOREIGN PATENT DOCUMENTS

| | | | |
|---|---|---|---|
| 428505 | 5/1991 | European Pat. Off. | 364/413.07 |
| 432138 | 6/1991 | European Pat. Off. | 364/413.07 |
| 611228 | 8/1994 | European Pat. Off. | |
| 9014850 | 12/1990 | WIPO | 210/646 |

OTHER PUBLICATIONS

"AK-10 System Operator's Manual for Hemofiltration" by Gambro, undated.

*Primary Examiner*—Joseph W. Drodge
*Attorney, Agent, or Firm*—John R. Ley

[57] ABSTRACT

A graphical operator machine interface for a dialysis machine and a method of graphically programming the dialysis machine involves graphically accessing substantially all typical machine operating and dialysis treatment parameters employed in a typical dialysis treatment, and graphically entering selections with respect to each of the selected parameters. The selections of the individual parameters establish display screens which individually present the selected parameters. The selections of the individual parameters also allow the operator to establish values for those selected parameters. The parameters include those involved for setup of the machine for dialysis treatment, those monitored during treatment, the alarm limits established during the treatment, and parameters which allow the automatic initiation of machine functionality prior to the use of the machine for treatments.

38 Claims, 19 Drawing Sheets

GRAPHICAL OPERATOR MACHINE INTERFACE AND METHOD FOR INFORMATION ENTRY AND SELECTION IN A DIALYSIS MACHINE

The present invention relates to a new and improved dialysis machine and method of graphically entering information for optimal control of a dialysis machine during treatment and of graphically presenting information for optimal monitoring of the patient and the dialysis treatment. More particularly, the present invention allows the operator to quickly and conveniently customize the dialysis machine for use in a flexible and optimal manner in regard to the particular dialysis treatment performed and the safety of the patient.

CROSS REFERENCE TO RELATED INVENTIONS

This invention is related to the invention described in a concurrently filed U.S. patent application for an Information Entry Validation System and Method for a Dialysis Machine, Ser. No. 08/484,015; a Single Microcontroller Execution of Control and Safety System Functions in a Dialysis Machine, Ser. No. 08/483,456; and a Technique for Automatically Preparing Dialysis Machine at a Predetermined Date and Time, Ser. No. 08/484,013. The disclosures of these applications are incorporated herein by this reference.

BACKGROUND OF THE INVENTION

In general, a dialysis machine is used as a substitute for the natural kidney functions of a human body. As such, the dialysis machine cleanses the blood of the natural accumulation of bodily wastes and separates the wastes from the blood outside of or extracorporeally of the body. The separated wastes are discharged, and the cleansed blood is returned to the body.

The wastes are separated from the blood in a dialyzer. The dialyzer includes an internal housing which is separated by a porous membrane into a blood side or compartment and a dialysate side or compartment. The blood removed from the patient flows through the blood side of the dialyzer. A prepared solution of dialysate is passed through the dialysate side of the dialyzer. The wastes from the blood pass through the membrane by osmosis, ionic transfer or fluid transport into the dialysate and, depending upon the type of dialysis treatment, desirable components from the dialysate may pass in the opposite direction through the membrane and into the blood. The transfer of the wastes into the dialysate cleanses the blood while allowing the desired components from the dialysate to enter the bloodstream.

As is apparent, the dialysis machine must be properly operated to perform effective dialysis in a safe and reliable manner. With the blood of the patient being removed and handled outside of the patient's body in an extracorporeal flow path, care must be taken that the treatment progresses safely and as is intended according to the dialysis prescription for the patient. With the patient's blood and the dialysate separated only by the dialyzer membrane, it is apparent that numerous safety concerns must be satisfied on a continual and reliable basis.

In the past most dialysis machines have provided very little opportunity for customized usage. With the complexity of the functions which must be performed during treatments, and the potential severity of the consequences if those functions are not properly and safely performed, the vast majority of the functionality of the machine has been preset. The operator was allowed to select only a few parameters, such as the target loss of weight or fluid volume to be removed from the patient during treatment, and the elapsed time for the treatment. More recently available dialysis machines have provided more optional parameters for operators to control. For example, more recent dialysis machines have provided the capability for the operator to vary the concentration of chemicals in the dialysate over the time period of the treatment.

One of the reasons for the lack of control over many of the operating parameters has been due to the complexity of the treatment and the potential for error if the operating characteristics are not carefully chosen. Dialysis machine manufacturers may have simply been unwilling to relinquish the control over the functionality of the system by making more of the operating parameters available for modification by the operator of the machine. Traditional medical treatment has also concerned itself with only a limited number of the functional aspects of the dialysis treatment. As a consequence, the typical dialysis machine provides only a limited number of operational parameters which the operator may select for modification, and only a limited number of operational parameters which can be displayed for monitoring the progress of the treatment and monitoring the condition of the patient.

Recent developments in the knowledge of the medical aspects of dialysis treatment have suggested that better results may be available by optimizing parameters during treatment that have not typically been optimized. Even from a non-therapeutic standpoint, many dialysis machine operators have begun to believe that more effective and safe treatment can be applied by closer and more individualized monitoring of the patient and the progress of the machine.

The relatively fixed functionality of the typical dialysis machine has proved to be a detriment to future modification of operating parameters. The operating parameters which the operator may desire to modify may not be modified due to the fixed functional aspects of the machine. If it is possible to modify certain parameters, the number of parameters which can be varied may be relatively limited. Further still, considerable difficulty may be encountered in attempting to modify those variables, particularly in computer-based dialysis machines. Few if any operators or maintenance personnel have the software programming capabilities that may be required to execute such changes. The inability to make these changes has potentially limited the treatment to levels which are not optimal to the patient. Furthermore the inability to vary significantly the operating parameters has discouraged attempts to optimize dialysis treatments, both from the therapeutic standpoint and from the patient comfort standpoint.

Similarly, the relatively fixed monitoring and information displaying capabilities of the dialysis machines have increased the responsibilities of the operator during treatments. In many circumstances, the information which the operator needs to monitor is not readily available, or is presented only in an awkward or difficult manner to easily comprehend. As a result the operator may not feel completely comfortable during the treatment, or the operator will avoid careful monitoring of the patient and machine conditions.

These and other considerations have contributed to the evolution of the present invention which is summarized below.

SUMMARY OF THE INVENTION

One of the significant aspects of the present invention pertains to a graphical information entry and display technique which simplifies access to a relatively large number of control parameters for the dialysis machine and a relatively large number of parameters which can be modified during the course of the treatment. Another significant aspect of present invention relates to substantially increasing the convenience and flexibility of accessing, modifying and displaying the parameters which may be useful or desirable in performing and monitoring a dialysis treatment with a dialysis machine. Still another important aspect of the present invention is to provide a maximum opportunity for optimizing therapeutic results from dialysis treatments by conveniently making a relatively large number of operating parameters equally accessible for modification in the dialysis treatment. Yet another important aspect of the present invention involves allowing the presentation of monitoring information in a manner which is optimally oriented to the convenience of the operator and the safety of the patient.

In accordance with these and other important aspects, the present invention can be generally summarized as a new and improved dialysis machine having a graphical operator machine interface (OMI), and a method of programming a dialysis machine. Both the OMI and the programming method generally relate to the features of graphically accessing substantially all typical machine operating and dialysis treatment parameters employed in a typical dialysis treatment, and graphically entering selections with respect to each of the selected parameters.

Preferably, a graphical screen is employed to present and enter information. The selected parameters are presented in a display screen which differs from the display screen in which all of the parameters were initially displayed. A further group of the selected parameters may be identified through the graphical screen, and values for those parameters entered. Entering the values for the identified parameters is accomplished through the graphical screen and a presentation of a value entry display screen. Substantially all of the parameters of utility or interest for a dialysis machine are available, including setup parameters, parameters to be monitored during the treatment, alarm limits parameters, and parameters allowing the automatic initiation of certain operational features of the dialysis machine prior to treatment.

The OMI and the graphical programming method provide convenience, accessibility and control with respect to the dialysis machine, the dialysis treatment, and the safety and condition of the patient to greatly facilitate dialysis treatments. Many other preferred aspects of the present invention, and a more complete appreciation of the present invention and its scope, may be understood from the accompanying drawings, which are briefly summarized below, from the following detailed description of a presently preferred embodiment of the invention, and from the appended claims.

DETAILED DESCRIPTION

Figure 1:
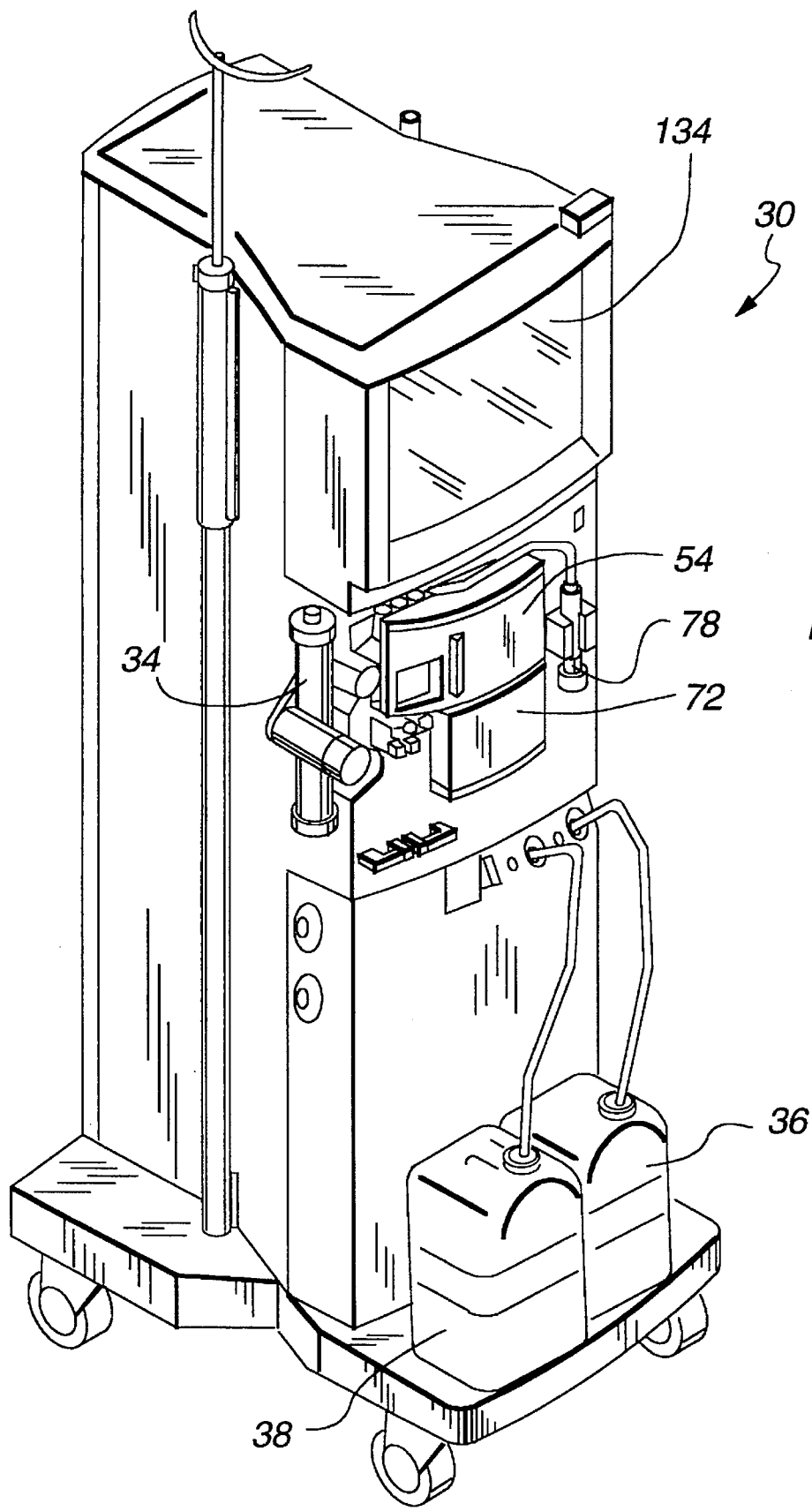
FIG. 1 is a perspective view of a dialysis machine which incorporates the present invention.

An example of a dialysis machine with which the present invention may be advantageously employed is shown at 30 in FIG. 1. The dialysis machine 30 includes the devices generally shown in FIG. 2, and those devices establish an extracorporeal flow path and a hydraulics flow path. The extracorporeal flow path conducts blood from a patient 32 to a dialyzer 34, and then returns the blood from the dialyzer 34 to the patient 32. The hydraulics flow path conducts dialysate from a supply 36 to the dialyzer 34, and then returns the used dialysate to a waste drain 38.

The blood in the dialyzer 34 is confined to a blood chamber 40, and the dialysate in the dialyzer 34 is confined to a dialysate chamber 42. The blood chamber 40 and the dialysate chamber 42 are separated by a microporous or other type of dialysis membrane or medium 44. The waste products contained in the blood within the blood chamber 40 are transferred through the medium 44 by osmosis, ionic transfer or flow transfer to the dialysate in the dialysate chamber 42. Desirable components of the dialysate in the dialysate chamber 42 may also be transferred to the blood in the blood chamber 40 by the same mechanisms. In this manner, the waste products are removed from the patient's blood, and the cleansed blood is returned to the patient 32. The used dialysate flowing from the dialysate chamber 42 discharges the waste products into the drain 38, which may be a public sewer.

The elements of the extracorporeal flow path include at least one blood pump 46 which controls the flow of blood from the patient 32. An arterial line or tubing 48 extends through an arterial clamp 50 to a blood handling cartridge 52. The blood handling cartridge 52 is normally retained behind a door 54 of the machine 30 when used. The blood handling cartridge 52 is not shown in FIG. 1. The blood pump 46 also is located behind the door 54 and adjacent to the cartridge 52. The blood pump 46 is typically a peristaltic pump in dialysis machines.

Blood flows through the arterial line 48 and into an arterial chamber 56 of the cartridge 52. The blood pump 46 draws blood from the arterial chamber 56 through a pump tubing 58 which is squeezed or pinched by a rotating rotor 60 against a stationary raceway 62, in the typical manner of peristaltic pumps. The blood within the pump tubing 58 which is rotationally in front of the rotor 60 is propelled through the pump tubing 58 and into a manifold 64 of the cartridge 52. A tubing 66 conducts the blood from the manifold 64 of the cartridge 52 into a blood inlet of the dialyzer 34.

The cleansed blood flowing from an outlet of the dialyzer 34 is transferred through a tubing 67 back to a venous chamber 68 of the cartridge 52. Blood from the venous chamber 68 is removed from the cartridge 52 through a venous tubing or line 70. Although not shown in FIG. 2, a venous blood pump similar to the arterial blood pump 46 may be located in the venous line to assist in forcing the blood back into the patient 32 or to regulate the flow of blood through the extracorporeal flow path. If employed, the venous blood pump is positioned behind a second door 72 of the dialyzer machine 30 shown in FIG. 1.

After leaving the venous chamber 68 the blood flows through the venous line 70 to an air detector 74. The air detector 74 derives signals related to any air in the venous line 70. If an excessive or dangerous amount of air is present, a venous line clamp 76 will immediately close to terminate the flow of blood through the venous line 70 before the air reaches the patient 32.

Because the blood in the extracorporeal flow path is prone to clot, a blood anticoagulant such as heparin is injected into the extracorporeal flow path. The anticoagulant is slowly delivered from a syringe 78 as a result of a linear driver mechanism (not shown) moving a plunger 80 into the syringe 78. Anticoagulant from the syringe 78 is introduced into the arterial chamber 56 of the cartridge 52 through a tubing 82. The syringe 78 and the linear driver mechanism are typically referred to as an anticoagulant pump.

The elements of the hydraulics flow path include a number of different valves (most of which are not shown) and a dialysate pump 84 which draws dialysate from the supply 36. The supply 36 is typically a container, an internal quantity of dialysate which the dialysis machine 30 has prepared from appropriate chemicals and a supply of purified water or an external supply delivered to the machine. The dialysate pump 84 draws the dialysate from the supply 36 and delivers it through a dialysate supply tubing or line 86 to an inlet of the dialysate chamber 42 of the dialyzer 34. The dialysate flows past the medium 44 where it absorbs the waste products from the blood in the blood chamber 40. Any beneficial components within the dialysate which are desired to be transferred to the blood pass through the medium 44 and into the blood in the blood chamber 40.

Prior to entering the dialyzer 34, the dialysate is heated in a heater 88 to the normal human body temperature. The temperature of the dialysate entering the dialyzer 34 should be at body temperature to avoid removing heat from the patient. Excessively warm dialysate will harm blood cells. Excessively cool dialysate will chill the patient. Temperature sensors (not shown) are located in the dialysate supply line 86 to monitor the temperature of the dialysate.

Conductivity sensors (not shown) are also present in the dialysate supply line 86 to measure the conductivity of the dialysate. The desired level of ionic transfer between the blood and the dialysate is achieved by predetermined conductivity characteristics of the dialysate.

The used dialysate containing the waste products is removed from the dialysate chamber 42 through a dialysate waste tubing or line 90 by operation of a drain pump 94. The dialysate containing the waste products is delivered by the drain pump 94 to the waste drain 38. The waste drain 38 may be a separate container which accumulates the used dialysate and accumulated waste products, or it may simply be a public sewer.

As a safety precaution bypass valves 96 and 98 are positioned at the inlet and the outlet of the dialysate chamber 42, respectively. The bypass valves 96 and 98 are connected by a bypass line 100. Normally the bypass valve 96 directs the inflow of dialysate into the dialysate chamber 42, and normally the bypass valve 98 directs the outflow of dialysate into the dialysate waste line 90. If a safety condition is detected, the bypass valves 96 and 98 are operated to their alternative, abnormal states, thereby directing the flow of dialysate through the bypass line 100, and bypassing the flow of dialysate around the dialyzer 34.

Figure 3:
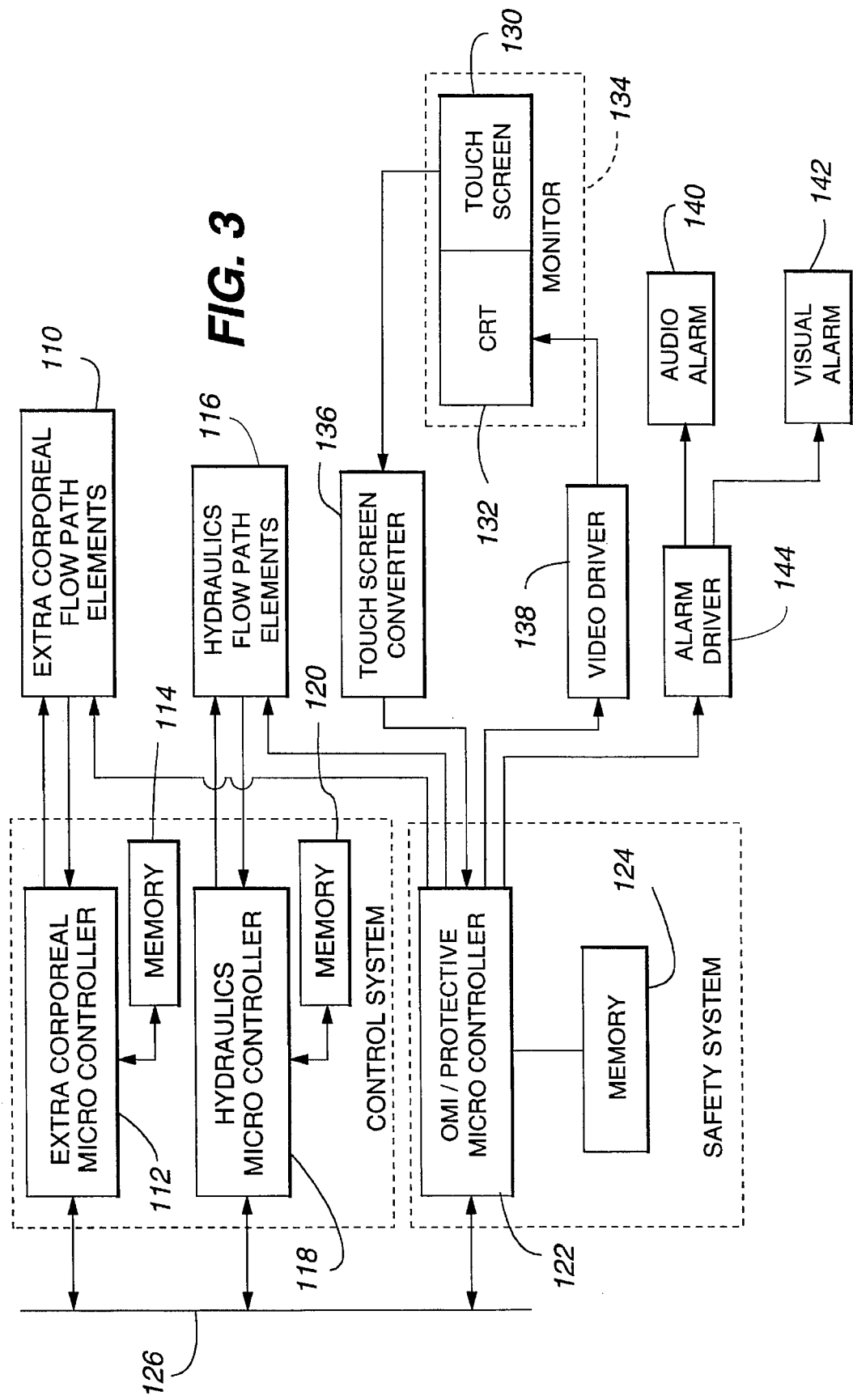
FIG. 3 is a block diagram of control and safety systems of the dialysis machine shown in FIGS. 1 and 2, illustrating the graphical OMI and the method of information entry and presentation according to the present invention.

The elements of the extracorporeal flow path, which have generally been described above, are shown and referenced generally at 110 in FIG. 3. The extracorporeal flow path elements 110 are controlled by an extracorporeal microcontroller 112 or other similar processing device, as shown in the systems diagram of FIG. 3. The extracorporeal microcontroller 112 executes a program recorded in a memory 114 to control the extracorporeal flow path elements 110.

The elements of the hydraulics flow path, which have generally been described above, are also shown and referenced generally at 116 in FIG. 3. The hydraulics flow path elements 116 are controlled by a hydraulics microcontroller 118 or other similar processing device. The hydraulics microcontroller 118 executes a program recorded in memory 120 to control the hydraulics flow path elements 116.

An operator/machine interface (OMI) and protective microcontroller 122 is also connected to the extracorporeal flow path elements 110 and the hydraulic flow path elements 116. The OMI and protective microcontroller 122 monitors the operating conditions in the extracorporeal and hydraulics flow paths, and upon detecting a potentially risky condition for the patient, assumes control over the extracorporeal and hydraulics flow path elements 110 and 116 to place the machine into a safe patient state. The protective microcontroller 122 executes a program recorded in its memory 124 to monitor the operating conditions of the dialyzer machine 30 and the conditions of the patient 32 during dialysis treatment, to determine a potentially hazardous condition, and to place the dialyzer machine in a safe patient state upon the detection of a hazardous condition.

The three microcontrollers 112, 118 and 122 communicate with one another to exchange information and confirm proper functionality, among other things, by use of a bus or network 126. In general, the extracorporeal microcontroller 112 and the hydraulic microcontroller 118 are generally responsible for the system management control functions of the dialysis machine. The protective microcontroller 122 is responsible for the safety functions of the dialysis machine.

The three microcontrollers meet the safety and governmental standards for dialysis machines. In general, the safety and governmental standards emphasize redundancy to avoid the possibility that a single equipment failure will place the patient in a hazardous condition. If the failure of one system management microcontroller occurs, the other safety system microcontroller is capable of placing the dialysis machine in the safe patient state. For example, should the hydraulics microcontroller 118 fail, the protective microcontroller 122 can assume control over the hydraulic flow path elements 114 to achieve the safe patient state. Similarly, should the extracorporeal microcontroller 112 fail, the protective microcontroller 118 will assume control over the extracorporeal flow path elements 110 to achieve a safe patient state. If the protective microcontroller 122 fails, the extracorporeal and hydraulics microcontrollers are capable of placing the dialysis machine in a safe patient state.

Although it is typical to use multiple microcontrollers in dialysis machines to meet the safety and governmental standards, a dialysis machine which meets safety and governmental standards but utilizes a single microcontroller for the system management and safety system functions is described in U.S. patent application for a Single Microcontroller Execution of Control and Safety System Functions in a Dialysis Machine, Ser. No. 08/483,456, filed concurrently herewith. The present invention may be utilized with either single or multiple microcontroller dialysis machines.

The present invention achieves a more convenient and natural approach to entering, selecting and presenting information into a dialysis machine, while simultaneously offering a substantially greater and more flexible opportunity to customize the dialysis machine for optimal patient treatment and optimal convenience of the operator in monitoring the machine and the patient during treatment.

The operator-machine interface (OMI) is the means by which information is entered into the dialysis machine, by which the operating parameter information is selected for modification or presentation, and by which the desired information is presented or displayed to the operator. The OMI functionality is incorporated with that of the protective microcontroller 122 as is shown in FIG. 3. By entering all information through the protective microcontroller 122, it is assured that the control system microcontrollers 112 and 118 will start with the same values or information which is initially recorded in the protective microcontroller 122.

The preferred means for entering and for displaying the entered information back to the operator is a conventional touch screen 130 attached to a front viewing surface of a conventional cathode ray tube (CRT) 132. The touch screen 130 and the CRT 132 are incorporated in a monitor 134 of the machine 30 shown in FIG. 1.

The touch screen 130 is a thin transparent sheet assembly which physically overlays a front viewing surface of the CRT 132. The overlaying relationship is generally illustrated in FIG. 3. With the touch screen 130 in position, the images displayed on the viewing surface of the CRT 132 define locations which the operator may select by applying finger pressure to the touch screen 130 at the location of the images. The touch screen 130 generates signals which describe the X-Y coordinates of the position where the finger pressure is applied. Those signals are supplied to a conventional touch screen converter 136 which converts the X-Y signals from the touch screen 130 into corresponding signals which are supplied to the protective microcontroller 122. The programmed functionality of the protective microcontroller 122 correlates the signals from the touch screen converter 136 with the location of the images displayed on the viewing surface of the CRT 132. The correlation is possible because signals are supplied by the protective microcontroller 122 to a video driver 138 to control the position and details of the images displayed on the viewing screen of the CRT 132. By correlating the X-Y position signals from the touch screen converter 136 with the viewing images defined by the signals delivered to the video driver 138, the microcontroller 122 is able to recognize those selections made by the operator touching the touch screen 130. This functionality is typical and well known for touch screen input and output (I/O) devices.

To alert the operator in the case of a safety or other condition, an audio alarm 140 and a visual alarm 142 are part of the dialysis machine 30. The audio and visual alarms 140 and 142 are controlled by a driver 144. The driver 144 responds to control signals supplied by the protective microcontroller 122. The protective microcontroller 122 delivers signals to the driver 144 to create a visual alarm or signal or an audio alarm or signal when necessary.

Figure 4:
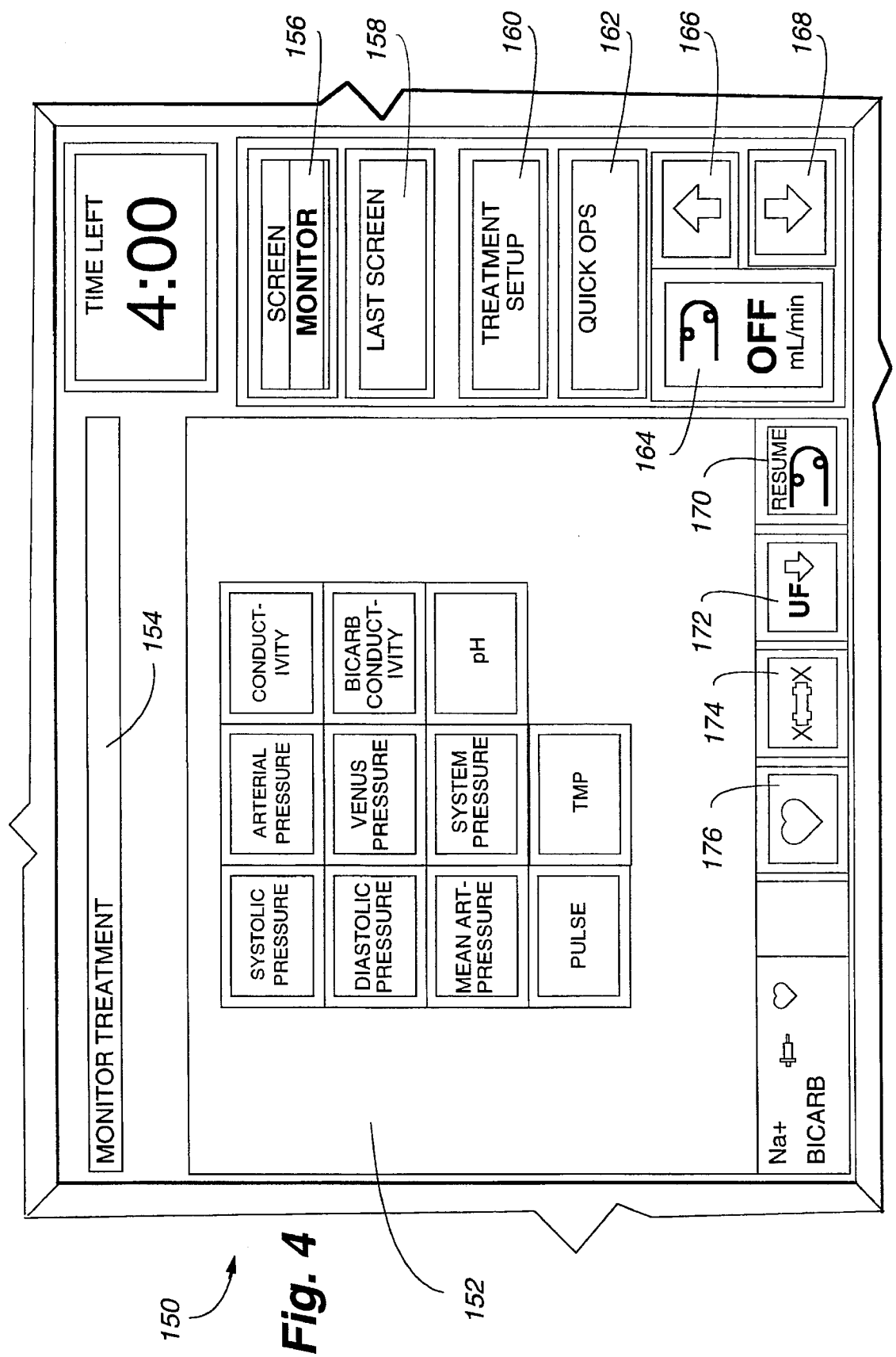
FIG. 4 is an illustration of a typical screen display presented on a monitor of the dialysis machine shown in FIGS. 1 and 3, when monitoring the machine and the patient during a dialysis treatment.

An example of a visual display created by the protective microcontroller 122 and the video driver 138 is shown in FIG. 4. The visual display shown in FIG. 4 is a typical presentation selected by the operator when monitoring the patient and the machine during treatment. The display appears on the viewing screen of the CRT 132, and it will therefore be referred to as a display screen 150. The display screen 150 is divided into different areas which present information concerning the functions and status of the dialysis machine. A relatively large main window area 152 shows a number of parameters which are being monitored during the treatment, in this example. A title bar 154 indicates that the parameters being monitored are shown in the main window 152.

In addition to the main window 152, the right-hand border or other designated area of the display screen 150 (as shown)

is occupied by images which allow the operator to select other display and functional features of the machine. Finger pressure at a screen image 156 allows the operator to index among various display options, and, for example, select the monitoring parameters, as is shown at 154 and 156. Pressing the touch screen above a last screen image 158 allows the operator to toggle between the present display screen 150 and the display screen which was previously displayed. Finger pressure above a treatment setup image 160 allows the operator to select and view a list of dialysis options that are expected with each treatment, for example, prime, start therapy, stop therapy, and the like. A quick OPS image 162 allows the operator to select and view in a relatively convenient manner, those optional parameters that are not necessarily accessed during the treatment.

The on and off operation of the blood pump 46 (FIG. 2) is controlled by finger pressure above blood pump icon or image 164. The blood pump is turned on and off with each finger contact. The rate of blood pump operation may be adjusted incrementally upward or incrementally downward by finger pressure on an up arrow image 166 or a down arrow image 168, respectively. Continual finger pressure on either of the arrow images 166 or 168 causes repeated incrementation. When operating, the blood pumping rate is displayed in the location where the word "off" appears in the blood pump image 164.

The bottom border or other designated area of the display screen 150 also includes a number of images or icons which represent control and monitoring conditions associated with the patient and the dialysis machine. The image at 170 which states "resume" is selected to resume operation of the blood pump operation if the blood pump has stopped.

The image at 172 which states "UF" accompanied by a downward pointing arrow is selected when it is desired to reduce the amount of ultrafiltration which may be occurring during a treatment. Ultrafiltration is a well-known aspect of some types of dialysis treatments which involves the direct introduction of an ultrafiltration solution into the blood. The ultrafiltrate may be introduced into the extracorporeal flow path prior to the blood reaching the dialyzer 34 (FIG. 2) or after the blood has passed through the dialyzer. Of course, if ultrafiltration is not used during the treatment, no functionality will be achieved by finger pressure above the ultrafiltration image at 172.

Figure 2:
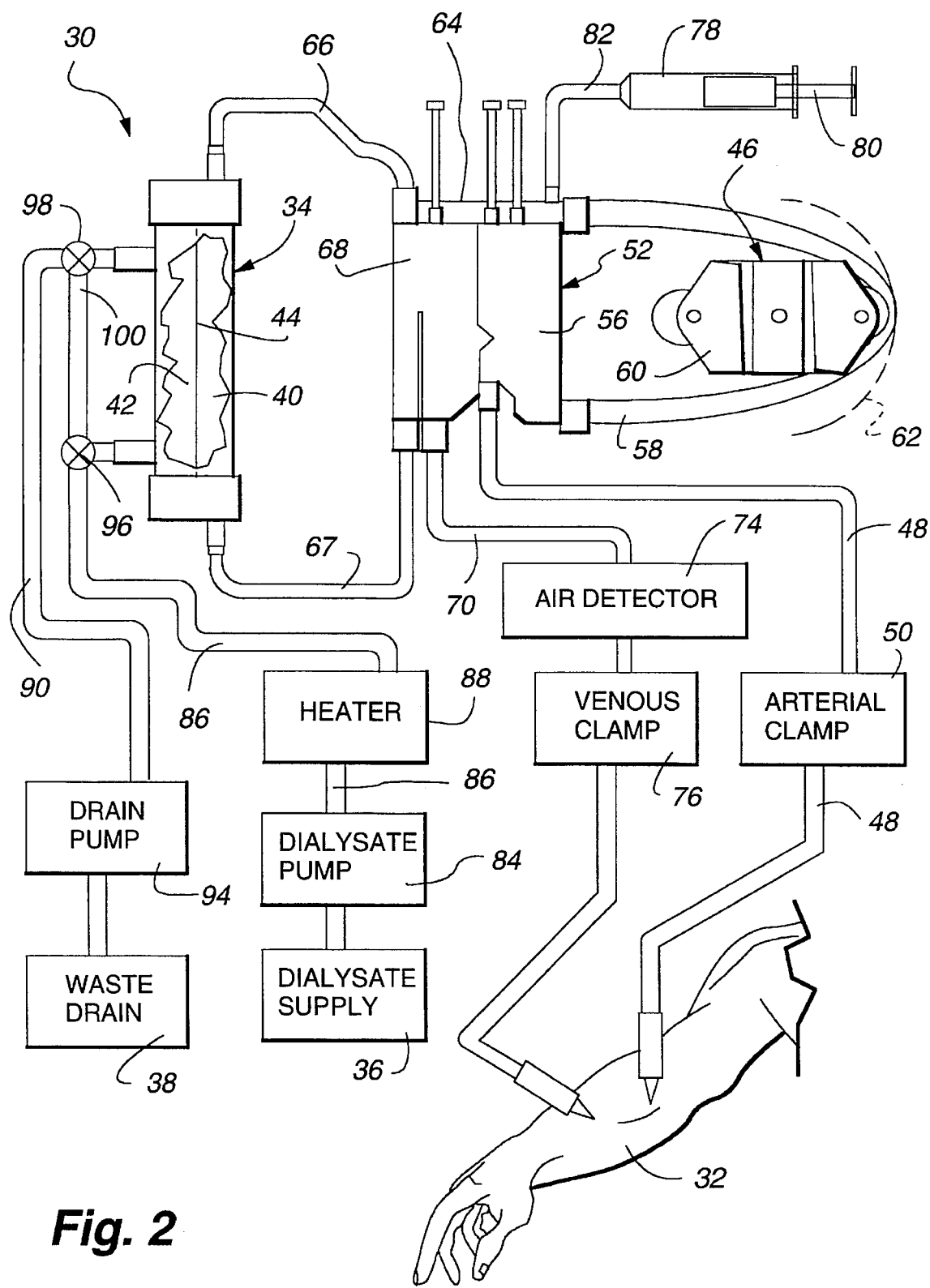
FIG. 2 is a generalized view illustrating a dialyzer, an extracorporeal flow path for blood from a patient through the dialyzer, and a hydraulics flow path for dialysate through the dialyzer, as are present during treatment of a patient with the dialysis machine shown in FIG. 1.

The image displayed at 174 is an icon representative of the function of bypassing the dialysate flow around the dialyzer 34 (FIG. 2). The dialyzer 34 is bypassed when the valves 96 and 98 divert the dialysis flow through the bypass line 100 (FIG. 2). Finger pressure above the bypassed dialyzer image 174 results in the immediate ability for the operator to achieve the safety condition of bypassing the dialyzer.

The image or icon of a heart at 176 allows the operator to instruct the dialysis machine to take a blood pressure reading from the patient. In order to take the blood pressure reading, the patient is connected to a typical blood pressure sensing cuff and the machine is equipped to automatically read and display the blood pressure reading obtained.

The basic template for the presentation of information at the display screen 150 is replicated in all of the display screens presented to the operator during setup, monitoring and other general use of the dialysis machine. The substantially consistent template for all of the display screens and the similar organization of the display screens allows a more convenient, time-conserving, reliable and safety-promoting approach to setting up, monitoring and using the dialysis machine.

One of the important improvements of the present invention is the customization of the information and the programming of the dialysis machine through use of the graphical information presented on the display screens. In general, the screens and the operator interaction with those screens are available to obtain substantially complete and convenient access to those parameters which control the operation of the dialysis machine, as well as equally complete and convenient access to those parameters which are desired to be monitored during the treatment. The access to the parameters is accomplished according to the needs and preferences of the operator, rather than as part of a fixed functionality established by the dialysis machine manufacture. As a result the dialysis machine is more conveniently and efficiently used according to the preference of the operator or the dialysis clinic, according to the particularized treatment prescribed for the patient, and possibly with additional comfort to the patient.

These important features of the present invention are obtained primarily through the operator machine interface (OMI) and the method of graphically selecting, presenting and programming control and monitoring information in the dialysis machine. The features of the improved OMI and the methodology of the present invention are described in FIGS. 5–20. The majority of the steps involved in practicing this invention are accomplished by the OMI/protective microcontroller 122 which executes the software program recorded in the memory 124 (FIG. 3). Some of the other steps are accomplished manually by the operator. Each of the steps shown in the flow charts of FIGS. 6, 8, 10, 11, 13, 14, 16, 18, and 20 are separately identified by reference numbers for convenience of description.

There are two important levels of customization available from the present invention. The upper level of customization represents the selection of parameters to be displayed or monitored, as well as the organization and presentation of a display screen to best represent those parameters. The second level of customization involves establishing and changing the values or quantities of those parameters. The second level of customization is principally described in the concurrently filed application for an Information Entry Validation System and Method for a Dialysis Machine, Ser. No. 08/484,015.

Figure 5:
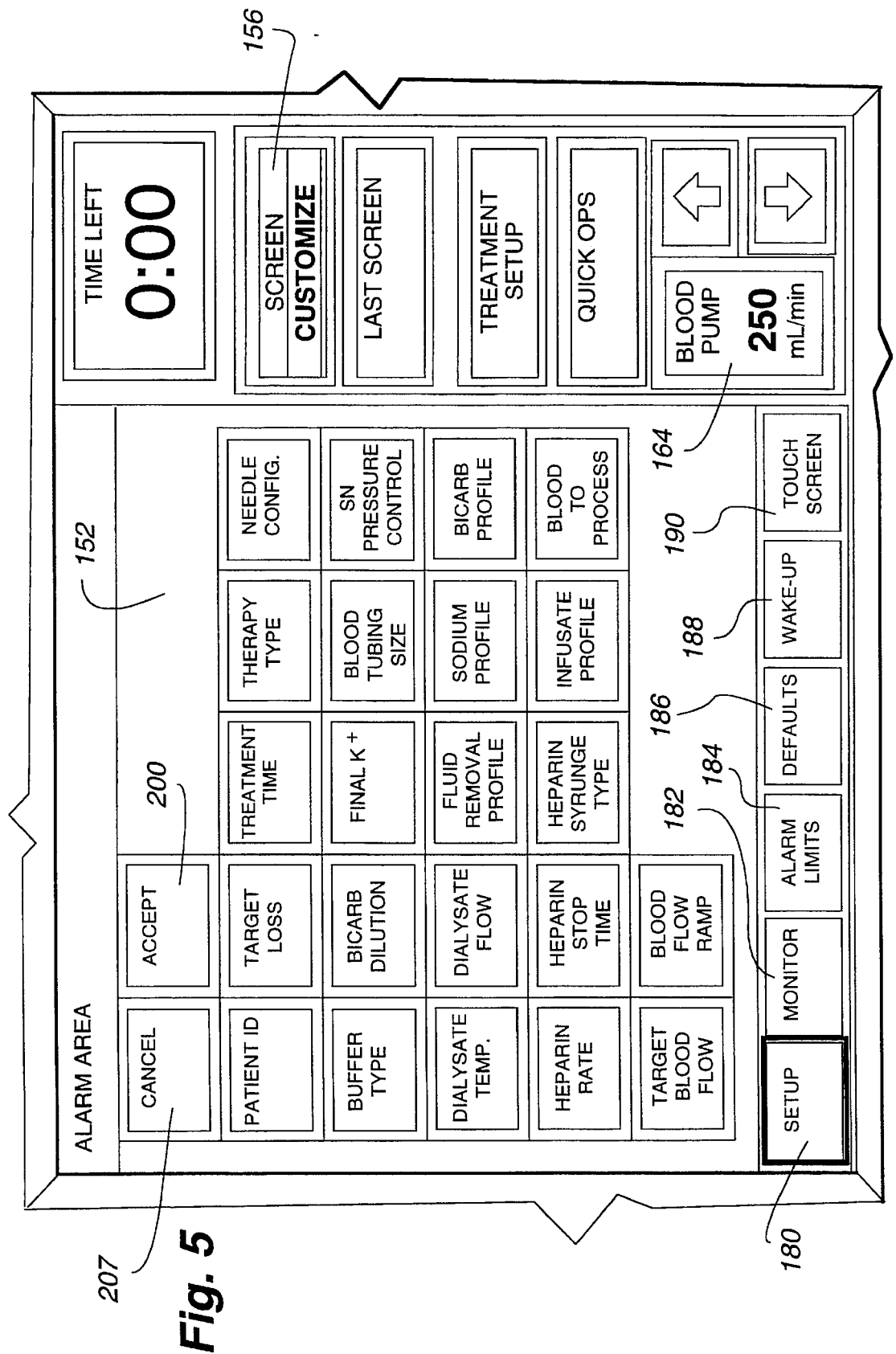
FIG. 5 is an illustration of a screen display of all setup parameters which may be selected for presentation in a customized setup display screen according to the present invention.
Figure 6:
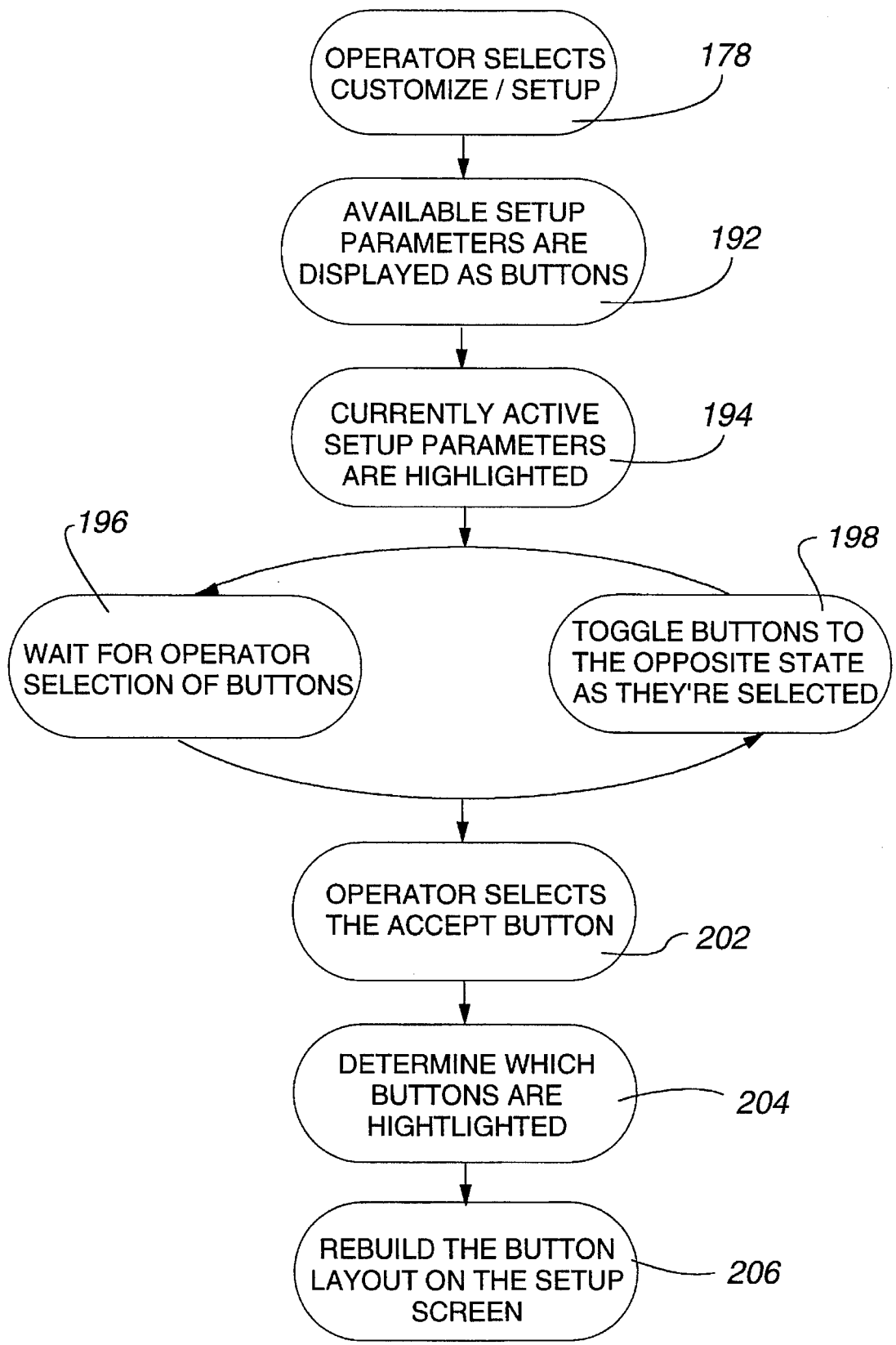
FIG. 6 is a flow chart of steps taken to select among the setup parameters shown in FIG. 5 and to present the selected parameters in a customized setup parameter display screen shown in FIG. 7.

The important graphical customization feature of the present invention of selecting the parameters to be presented for programming and monitoring the machine is initiated by the operator touching the screen button 156, as shown in FIGS. 5 and 6. Repeated touches to the screen button 156 present different screen options until the Customize option is presented at 178. The Customize option is highlighted at the bottom portion of the screen button 156, as is shown. The bottom border area of icons and images at 170, 172, 174 and 176 shown in FIG. 4 is replaced by the features which may be customized. Those features shown in FIG. 5 are the setup parameters represented by a Setup button 180, the parameters to be monitored represented by a Monitor button 182, the alarm limit parameters represented by an Alarm Limits button 184, all of the default parameters available from the machine represented by a Defaults button 186, an automatic operation described more particularly in the concurrently filed application for a Technique for Automatically Preparing Dialysis Machine at a Predetermined Date and Time, Ser. No. 08/484,013, in which the dialysis machine automatically initiates a clean and disinfection operation prior to dialysis treatments, represented by a Wake-Up button 188, and an operation in which the location of finger pressure on the touch screen 130 (FIG. 3) is calibrated to the images presented, represented by a Touch Screen button 190.

The setup button 180 has been touched and as a result is highlighted as shown in FIG. 5. The selection of the setup button 180 results in the presentation of all setup parameters available in the main window 152. All of the parameters shown in the main window 152 are available for selection by the operator. Generally, setup parameters are those which control the operation of the dialysis machine during treatment. The quantities associated with each of these parameters will generally need to be adjusted by the operator prior to each treatment, or must be confirmed by the operator prior to treatment.

Many of the setup parameters shown in the main window 152 in FIG. 5 are not relevant to the majority of dialysis treatments, and therefore need not be dealt with before each treatment. However, the ability to access those parameters and thereafter adjust each of them allows the machine to be uniquely adjusted for special therapeutic results when prescribed by a physician, or as may be necessary to obtain an optimal response from the patient. The convenience of accessing all of these parameters from a single screen is a substantial convenience and advantage to the machine operator.

The list of parameters which are presented as shown in FIG. 5 and at step 192 in FIG. 6 is conceivably any variable of operation of the dialysis machine. The list of parameters shown in FIG. 5 is presently considered to be the most useful group. Those parameters include the Patient ID, which represents a number or other identification assigned to a patient. The patient identification number is frequently used by dialysis clinics to record the specific treatment information and results to specific patients. The Target Loss parameter describes the weight or volume of waste which is desired to the removed from the patient during the treatment. The Treatment Time is the time allotted for the treatment. The Therapy Type refers to the type of therapy which may be performed. Examples of dialysis therapy treatments are hemodialysis, isolated ultrafiltration and hemodiafiltration. Other types are also known. The Needle Configuration parameter refers to whether a single needle or a double needle dialysis treatment is performed. A double needle treatment is illustrated in FIG. 2. A single needle treatment involves withdrawing blood from the patient and returning blood to the patient through a single needle, with the withdrawal and return flows occurring in a forward and backward flow manner.

The Buffer Type parameter relates to the type of buffer solution used in the dialysate. Typical buffers are acetate and bicarbonate. The Bicarbonate Dilution describes the dilution ratio of bicarbonate to acid used in the dialysate. The Final K+ parameter relates to the concentration of potassium in the dialysate. The Blood Tubing Size relates to the size of the pump tubing 58 (FIG. 2) used in the blood handling cartridge. The size of the pump tubing is important because it determines the volume of blood which is transferred by the blood pump rotor with each rotation. The SN Pressure Control parameter relates to the pressure limits for the differential pressure transitions that are employed to push blood into the patient and withdraw blood out of the patient with a single needle dialysis treatment.

The Dialysate Temperature parameter relates to the temperature of the dialysate supplied to the dialyzer. The dialysate temperature is established by the heater 88 (FIG. 2). The Dialysate Flow parameter describes the flow rate of dialysate through the dialyzer. The Fluid Removal Profile parameter describes the rate of fluid removed from the patient relative to time. The profile may be a constant rate during the treatment time, a combination of different rates, variable rates over the treatment time, or one or more step function increases over the treatment time. The Sodium Profile describes the sodium content of the dialysate over time. The variability of that rate may include all of the functions described with respect to the fluid removal profile. The Bicarbonate Profile also describes a function of the bicarbonate in the dialysate relative to the treatment time.

The Heparin Rate parameter describes the rate of delivery of heparin from the syringe 78 (FIG. 2) during the treatment time. The heparin rate may be constant or it may also be a variable function of time and have its own profile. The Heparin Stop Time parameter describes the time in the treatment where the delivery of heparin is terminated. Toward the end of a dialysate treatment the heparin delivery is typically terminated, because the patient's blood is reasonably well anticoagulated by that time. The Heparin Syringe Type parameter is intended to describe the size of the syringe used. The Infusate Profile parameter describes the rate of delivery of infusate to the bloodstream in a function which varies with the treatment time. Again, the infusate profile may take a variety of rates and functions relative to time. The Blood to Process is a parameter that describes the quantity of blood processed. This parameter may be set or used as the primary determinant of the length of the treatment.

The Target Blood Flow parameter describes the desired blood flow rate through the extracorporeal flow path. The Blood Flow Ramp describes the variability in the blood flow rate relative to the time of the treatment. This ramp effect is similar to a profile where the rates may change as a function of time.

After the parameters shown in FIG. 5 have been selected by touching the setup button 180, which becomes highlighted after being touched, the operator thereafter selects those parameters which the operator wishes to establish for each treatment, or for the individual treatment to be performed next. Selection of the parameters is obtained by touching the button or area of the display screen where the variable is displayed. Those currently active parameters are highlighted, as shown at 194 in FIG. 6. The highlighted parameters which the operator desires to select need not be touched again, because those parameters have been previously selected.

The OMI waits for the operator to begin selecting buttons by touching the images, as shown at 196. Those parameters which have previously been selected may be de-selected by touching the highlighted parameter. The touch causes a toggling effect on both the highlighted and the non-highlighted buttons. Parameters not previously selected are selected by touching the non-highlighted button, and parameters previously selected which are desired to be de-selected are touched in their highlighted buttons. The resulting toggling effect achieves the selection or de- selection, as shown at 198. Of course, those previously selected parameters which are to remain selected are not touched since the previous selection will continue until toggled into the opposite state of selection.

Once the operator has selected all of the parameters to be displayed an Accept button 200 (FIG. 5) is touched at 202 (FIG. 6). The touch to the accept button 200 is interpreted as the final selection by the operator, and thereafter the highlighted parameters are determined by the OMI at 204 (FIG. 6). The display screen is rebuilt or restructured to present only the selected parameters as shown at 206 in FIG. 6 and in the display screen 150 in FIG. 7.

If the operator is not satisfied with the selections, a cancel button 207 (FIG. 5) is touched. All previous selections are de-selected, and the process flow reverts back to step 192 (FIG. 6). Starting back at step 192 starts the sequence of customizing the setup parameters in the manner just described.

Figure 7:
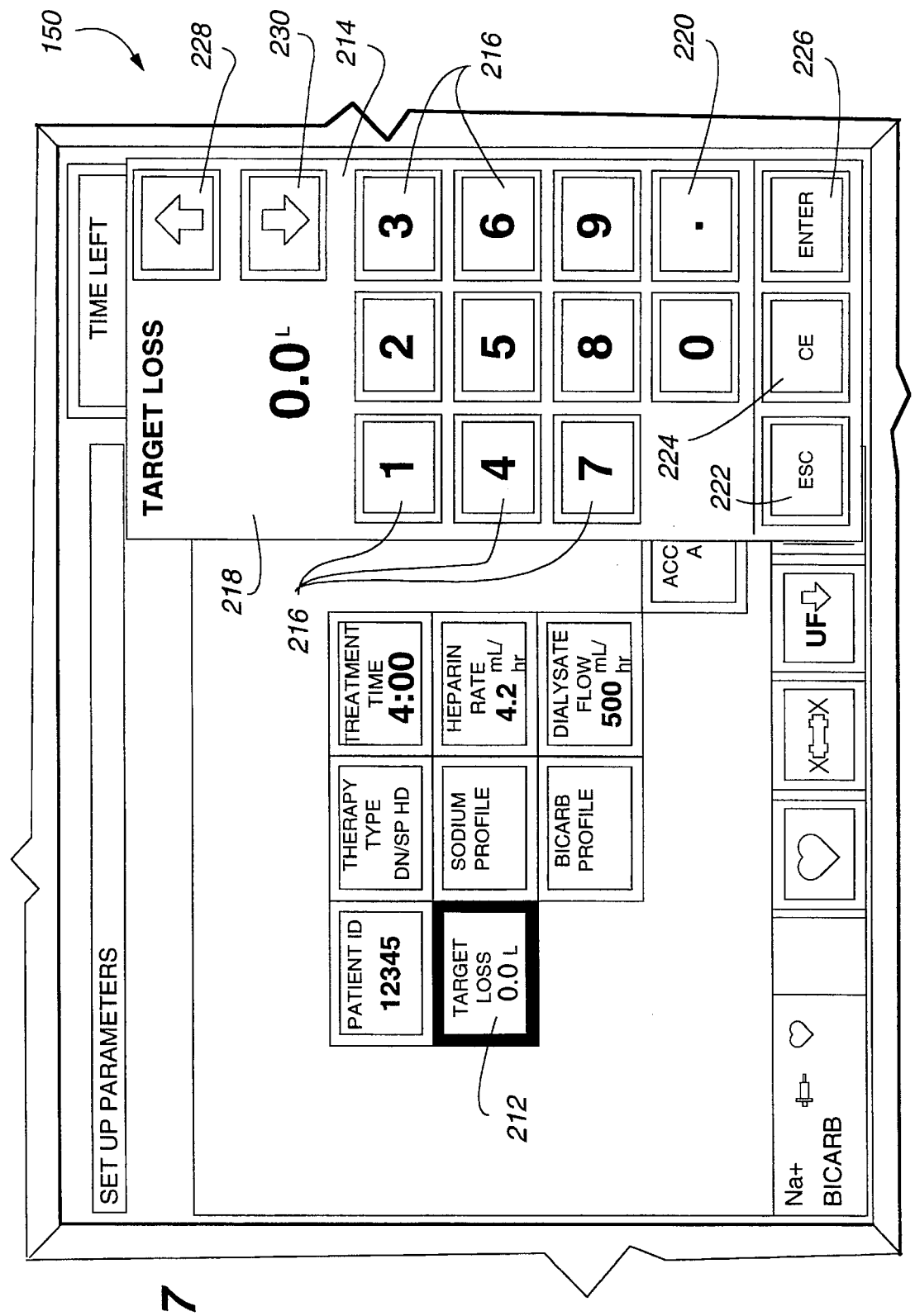
FIG. 7 is an illustration of a customized setup parameter display screen showing the selected setup parameters obtained from the actions shown in FIG. 6, and a pop-up keypad used to change the values of the parameters shown.

The display screen 150 shown in FIG. 7 contains eight of the setup parameters in the main window 152 which were selected by the process described in conjunction with FIGS. 5 and 6. Once the setup parameters have been selected and the screen rebuilt as shown in FIG. 7, the individual values or quantities associated with each setup parameter may be adjusted. The adjustment process is described in greater detail in the concurrently filed application for an Information Entry Validation System and Method for a Dialysis Machine, Ser. No. 08/484,015, but those processes are generally summarized in conjunction with FIGS. 7 and 8.

Figure 8:
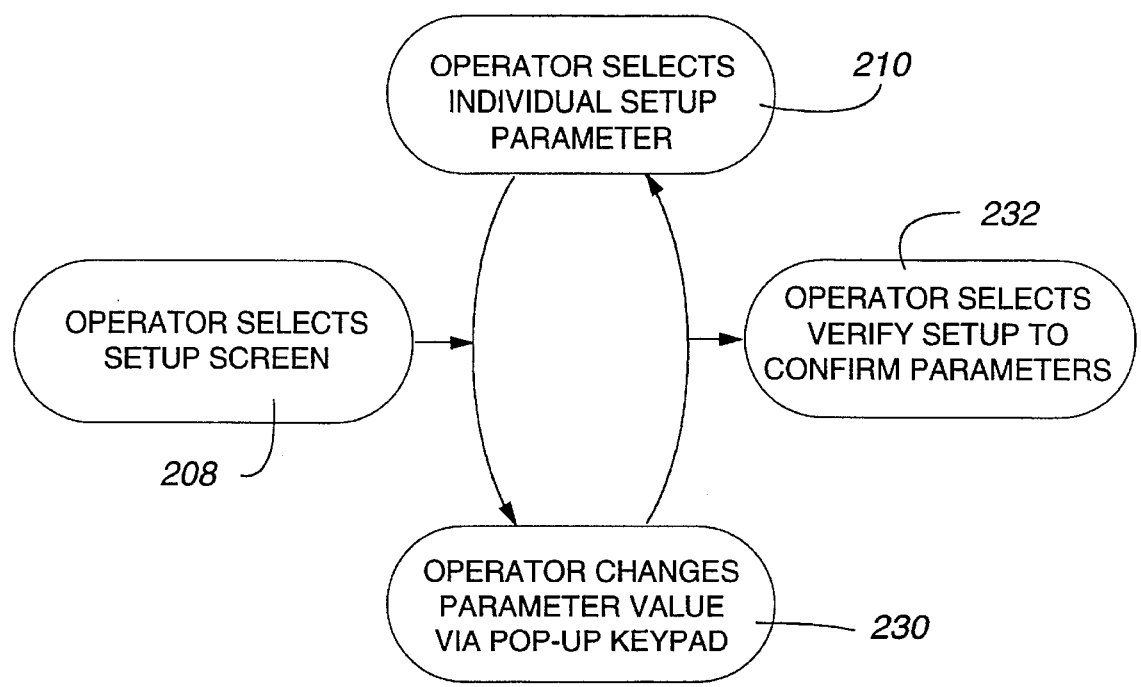
FIG. 8 is a flow chart of steps taken to modify or establish the values for the setup parameters selected as shown in FIG. 7.

To change the quantity or value of a setup parameter as shown at 208, the parameter whose value is to be changed is touched at 210 as shown in FIG. 8. The Target Loss parameter button 212 has been touched and becomes highlighted in the example shown in FIG. 7. Upon selecting the parameter, a pop-up keypad 214 appears on the display screen 150. The signals which define the keypad display 214 are created by the microcontroller 122 and the video driver 138 (FIG. 3), and the CRT 132 (FIG. 3) creates the keypad display 214. The keypad display is presented in place of some of the images which otherwise occupy the right hand and bottom border areas of the display screen 150, as can be seen by comparing FIGS. 4 and 7.

The keypad display 214 includes a number of different areas. These areas define numeric buttons 216, a selected parameter display area 218 which presents a title corresponding to the parameter selected at 212, a decimal point button 220, an escape button 222, a clear button 224, and an enter button 226. In addition, an up arrow 228 and a down arrow 230 are located adjacent to the display area 218 for the purpose of incrementing the value of the parameter shown in the display area 218, either upwardly or downwardly.

After the keypad at 214 is displayed, the operator changes the value of the highlighted parameter using the keypad as shown at 230 in FIG. 8. The operator continues selecting the parameters and changing the values of those parameters as shown at 210 and 230 in FIG. 8 until all of the values have been changed to the satisfaction of the operator. Once acceptable, the operator verifies all of the values established for all of the selected parameters as shown at 232 in FIG. 8. The operator verifies the values by touching the enter button 226 (FIG. 7).

The improved graphical functionality of the OMI and the method of selecting and entering information for the setup parameters described in conjunction with FIGS. 4–7 represents the two levels of customization available from the present invention. The first level of customization allowed the operator to conveniently access and select those operational parameters which were desired to control and optimize the treatment. The final setup parameter display screen (FIG. 7) presents those selected parameters in a clear and easy to comprehend manner. The second level of customization allows the values of each parameter to be adjusted, again in a convenient and easy to comprehend manner. As a result, the optimal conditions for both the operator and the patient are easily obtained.

Figure 9:
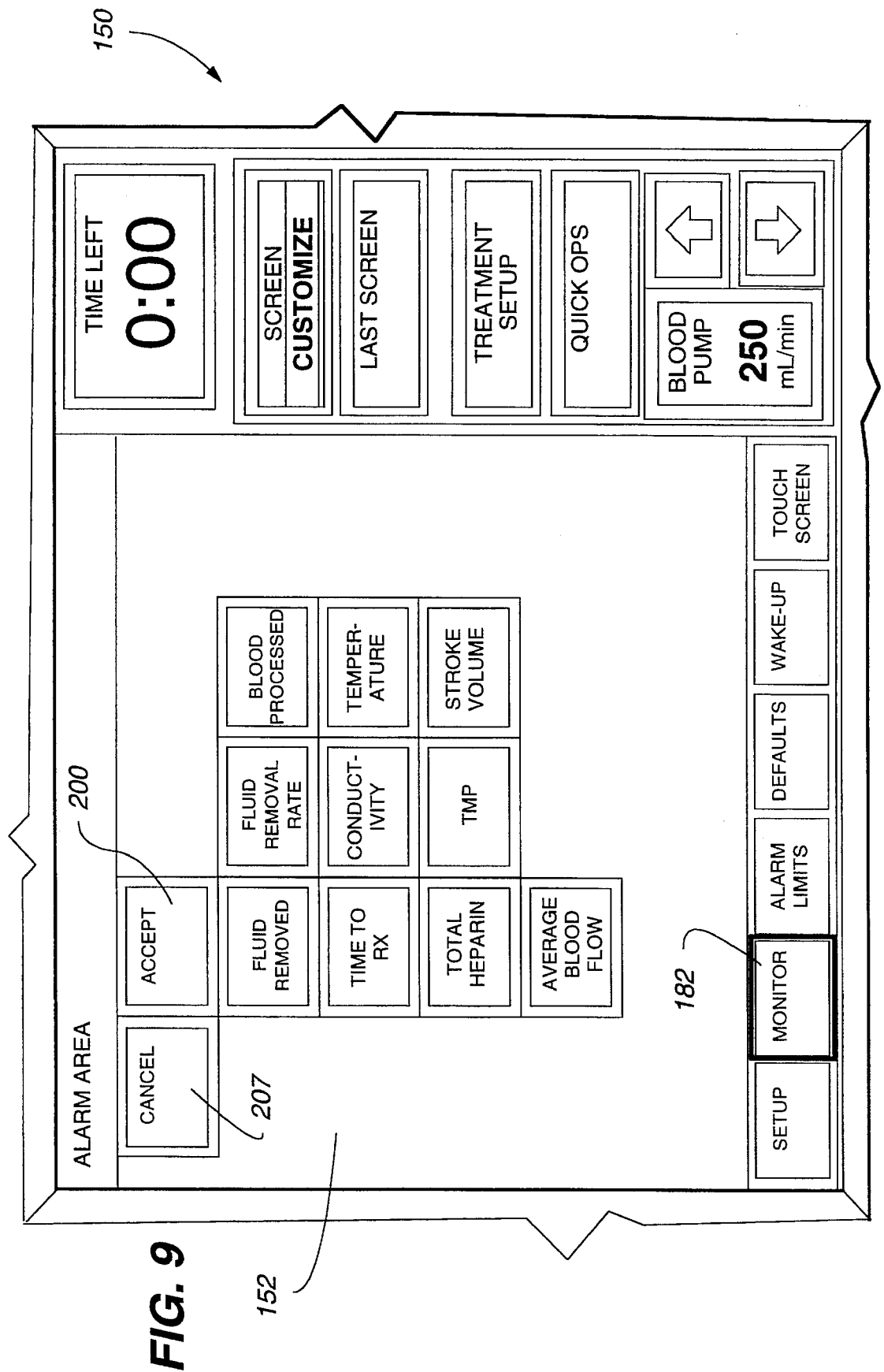
FIG. 9 is an illustration of a display screen of monitoring parameters which may be selected for presentation in a customized monitoring parameter display screen according to the present invention.
Figure 10:
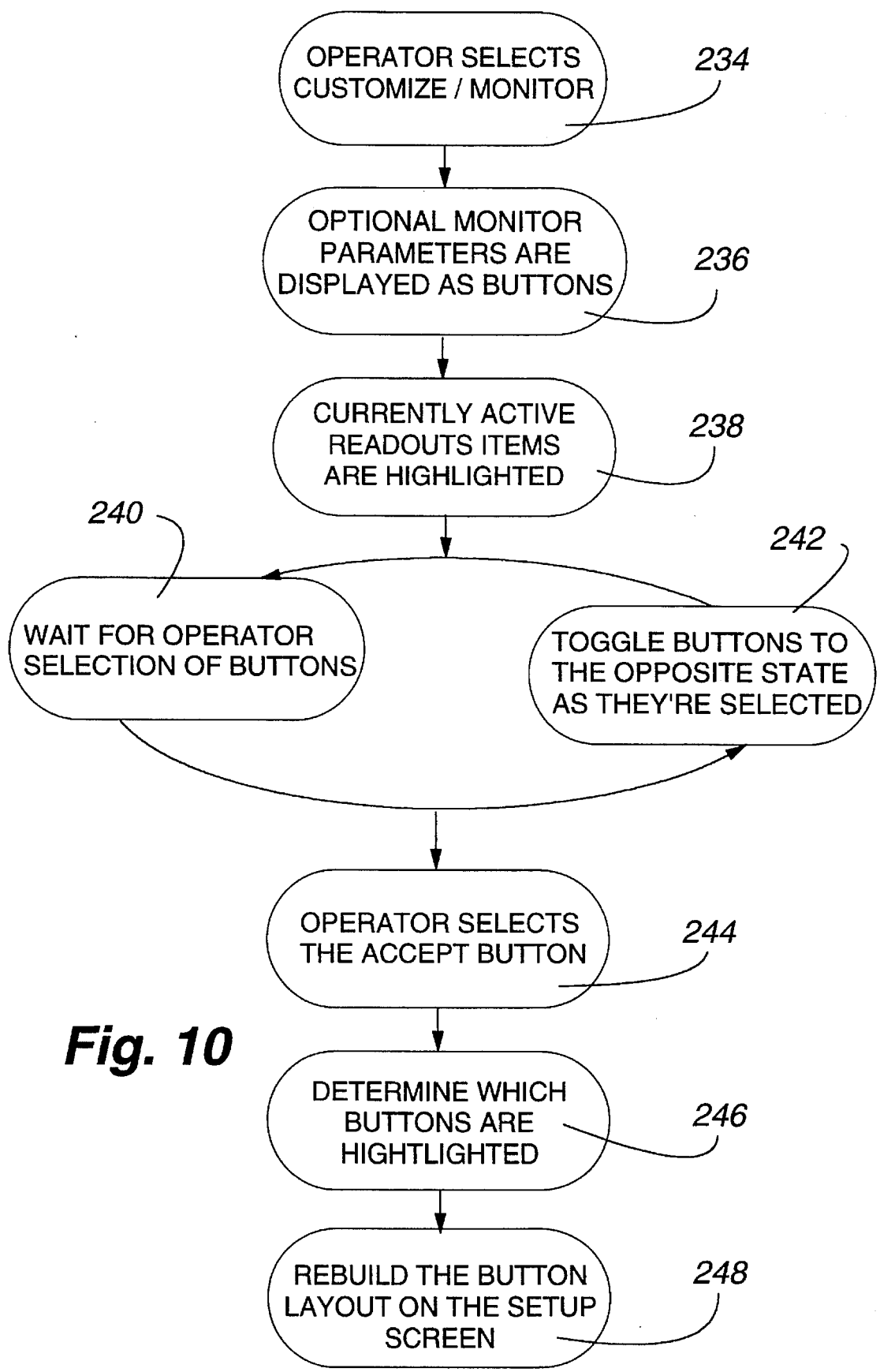
FIG. 10 is a flow chart of steps taken to select among the monitoring parameters shown in FIG. 9 and to present the selected parameters in a customized monitoring parameter display screen.

Various monitoring parameters can also be selected for monitoring during treatment, as shown in FIGS. 9 and 10. The monitor button 182 is touched as shown in FIG. 9 and it becomes highlighted. Touching the monitor button 182 constitutes a selection of the customizing function for the monitored parameters as shown at step 234 in FIG. 10. All of the optional monitor parameters are then presented in the main display window 152 (FIG. 9) as a result of the step 236 (FIG. 10). The currently effective ones of the monitoring parameters are highlighted in the display as a result of the step 238 (FIG. 10).

Those monitoring parameters which have previously been selected are highlighted. Those previously highlighted parameters which the operator no longer wishes to monitor are de-selected by touching the highlighted button, thereby toggling the highlighted parameter into a de-selected state. Similarly, those monitoring parameters which were not previously selected are selected by touching the non-highlighted button. Touching the highlighted and non-highlighted buttons in this manner constitute the selection of the buttons shown at step 240 (FIG. 10), and the toggling of the selected and de-selected monitoring parameters is shown at step 242.

Substantially all of the monitoring parameters which could be of reasonable interest to the operator are presented for selection, as shown in FIG. 9. Those monitoring parameters include the Fluid Removed and the Fluid Removal Rate. Both of these parameters relate to the waste fluid removed from the patient's blood. The Blood Processed monitoring parameter relates to the quantity of blood which has been passed through the dialyzer. The Time to Rx monitoring variable is the remaining time in the treatment. The Conductivity is a characteristic of the dialysate. The Temperature also refers to the dialysate temperature. The Total Heparin describes the total quantity of heparin delivered to the patient during the treatment. The THP monitoring parameter refers to the "trans-membrane pressure." The TMP is the pressure differential across the dialyzer medium 44 between the blood chamber 40 and the dialysate chamber 42 (FIG. 2). The TMP is monitored to evaluate the effectiveness of the medium and to identify a condition under which the medium may become obstructed to the flow through it. The Stroke Volume monitoring parameter relates to the volume of ultrafiltrate delivered by an ultrafiltration pump during ultrafiltration dialysis treatments, or to the volume of sterilant delivered by a sterilant pump during disinfection of the hydraulics flow path. The Average Blood Flow monitoring parameter describes the average blood flow rate through the dialysis machine during the course of the treatment. Of course other monitoring parameters could be displayed if those parameters are useful to the operator and available in the dialysate machine.

Once all of the monitoring parameters have been established as desired by the operator, the operator accepts those monitoring values by touching the accept button 200 (FIG. 9) at the step 244 (FIG. 10). Activation of the accept button at step 244 causes the OMI to determine which of the monitoring parameters has been selected as shown at step 246. Thereafter those selected monitoring parameters are rebuilt and displayed in the main window area 152 of the display screen 150 (FIG. 9) by the step 248 (FIG. 10).

If the operator is not satisfied with the selected monitoring parameters, the operator may touch the cancel button 207, causing the program flow to revert back to the step at 236. The entire program flow for selecting monitoring parameters to be presented can thereafter be started again.

Figure 11:
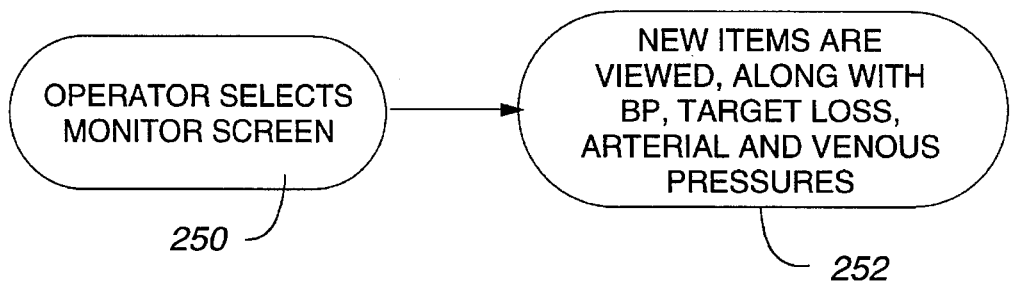
FIG. 11 is a flow chart of steps taken to display the customized monitoring parameter screen display established by the steps shown in FIG. 10 and to display the values of the selected monitoring parameters.

After establishing the monitoring parameters, the operator will simply observe those parameters during treatment as shown in FIG. 11. Monitoring the parameters begins with the operator selecting the monitor screen shown at step 250. The previously selected monitoring parameters are thereafter displayed as shown at step 252. Because monitoring is occurring, there are no values to set or modify. The values of the monitoring parameters are simply displayed. Therefore the second level of customization available for setting or modifying the selected parameters is not available for the monitoring parameters.

Figure 12:
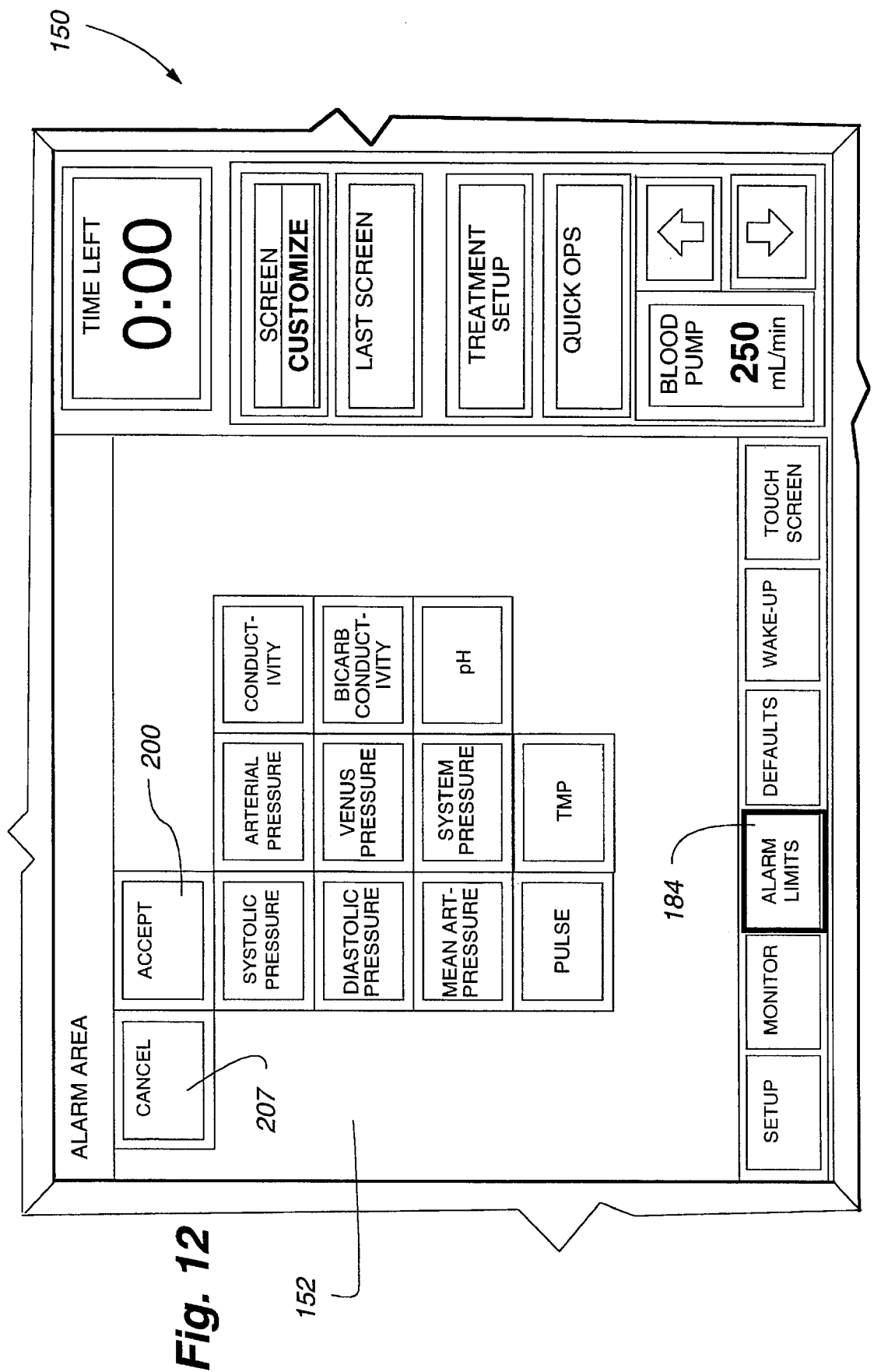
FIG. 12 is an illustration of a display screen of alarm limits parameters which may be selected for presentation in a customized alarm limits parameter display screen according to the present invention.
Figure 13:
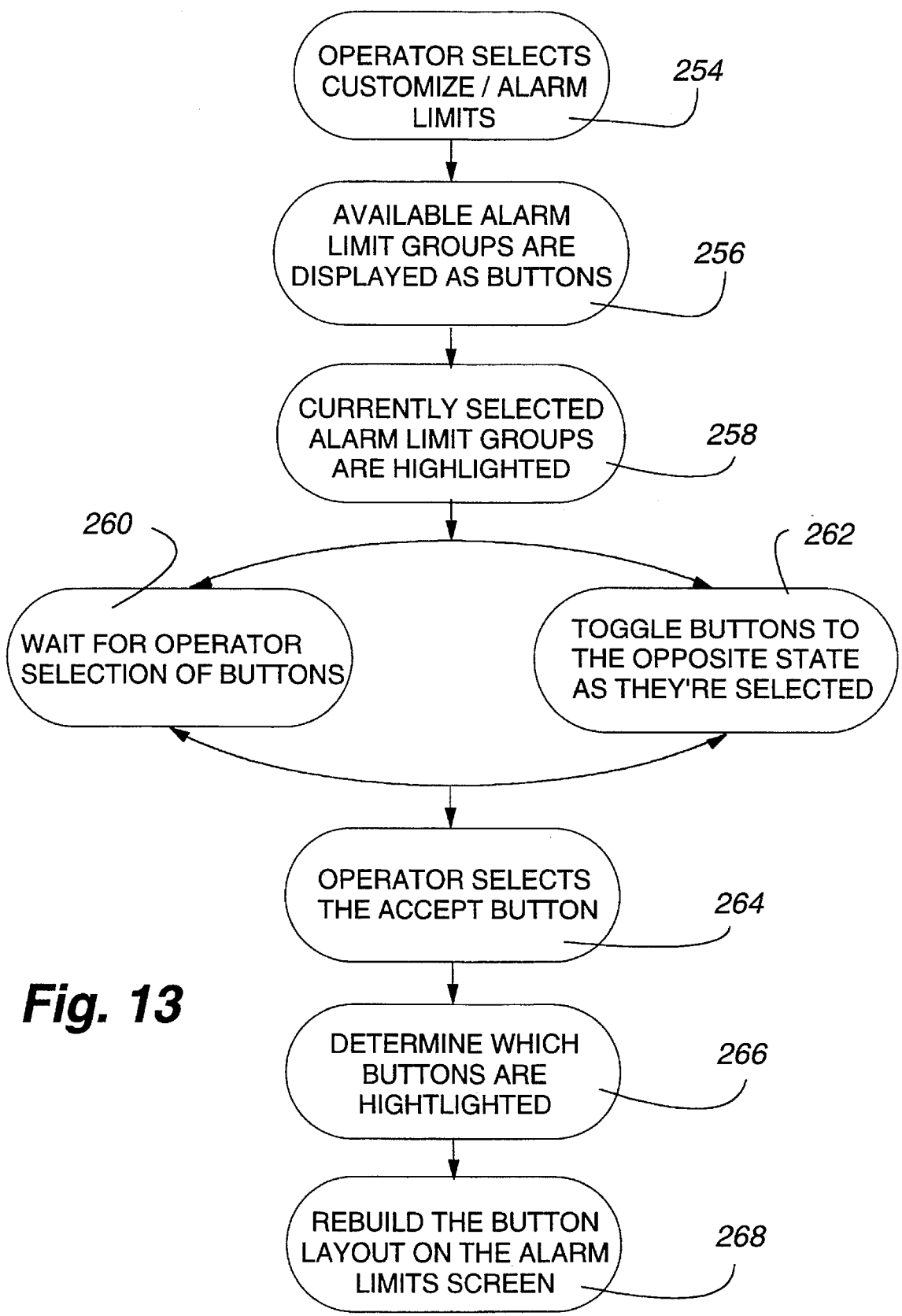
FIG. 13 is a flow chart of steps taken to select among the alarm limits parameters shown in FIG. 12 and to present the selected parameters in a customized alarm limits parameter display screen.

Various alarm limits parameters can be selected for a customized screen display by touching the alarm limits button 184 as shown in FIG. 12 and at the step 254 in FIG. 13. The available alarm limits parameters are displayed at step 256 (FIG. 13) in the main display window 152 of the screen display 150 (FIG. 12).

The currently selected alarm limits parameters are highlighted and those de-selected alarm limits parameters are not highlighted as shown at step 258. The operator selects those non-highlighted alarm limits parameters by touching the alarm limits parameter buttons desired. The operator also de-selects those active alarm limits parameters by touching the highlighted alarm limits parameter buttons. Touching the highlighted and non-highlighted parameter buttons changes the states of the selected parameter from active to not-active and from not-active to active, as the case may be. Touching the alarm limits buttons selects them as shown at step 260 (FIG. 13) and also toggles the state of the selected alarm limits parameter as shown at step 262.

The types of alarm limits available to be monitored include all of those typical and relevant ones used in dialysis. For example the main alarm limits shown are the Systolic Blood Pressure, the Diastolic Blood Pressure and the Mean Arterial Blood Pressure of the patient; the Arterial Pressure, the Venous Pressure and the System Pressure within the extracorporeal flow path; the Conductivity of the dialysate; the Bicarbonate Conductivity of the dialysate; the pH of the dialysate; the patient's Pulse rate; and the TMP or trans medium pressure in the dialyzer. Other alarm limits parameters could include the temperature of the dialysate.

Once all of the desired alarm limits parameters have been selected and are acceptable to the operator, the accept button 200 (FIG. 12) of the display screen is touched as shown at step 264 (FIG. 13). Thereafter the OMI determines which of the available alarm limits parameters have been selected at step 266, and the customized alarm limits display screen is presented at step 268.

Figure 14:
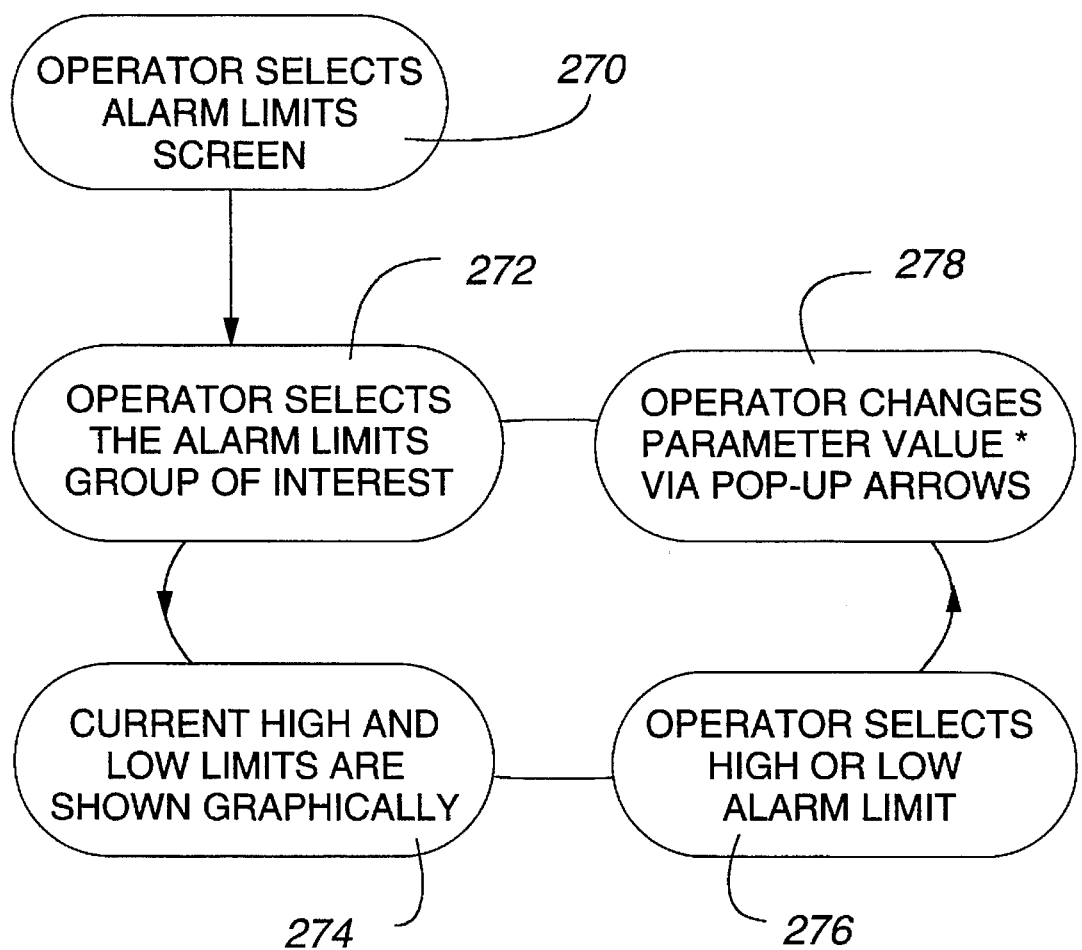
FIG. 14 is a flow chart of steps taken to modify or establish the values for the alarm limits parameters selected as shown in FIG. 13.

Because some of the alarm limits parameters may be adjusted or established by-the operator or the dialysis clinic, the second level of establishing or modifying the alarm limits parameters is available to the operator as shown in FIG. 14. Initiation of the procedure for modifying or establishing values for the alarm limits parameters begins at step 270 where the operator has selected the alarm limits screen. The values associated with the selected alarm limits parameters will be displayed in the alarm limits parameters buttons, in a manner similar to that shown for the setup parameters in FIG. 7. In addition a keypad will also be presented on the display screen. A touch to the alarm limits parameter of interest highlights that alarm limit parameter and makes its value available to be established or modified, as shown at step 272. Thereafter the high and low limits for the selected parameter are displayed graphically as shown at step 274. The operator then selects one of the high or low limits at step 276 and modifies that value at step 278. The steps 272, 274, 276 and 278 are repeated until all of the alarm limits and the values associated with each alarm limit is established or modified to the satisfaction of the operator.

The OMI/protective microcontroller 122 (FIG. 3) checks the values which the operator enters at step 278 against established acceptable limits before the operator is allowed to accept those entered values. An evaluation of the entered value relative to an acceptable range of values assures that the operator can not program the machine in an unsafe manner.

With the alarm limits parameters selected and displayed in the customized alarm limits parameter display screen and the values established for those alarm limits, the dialysis machine is adjusted for optimal efficiency in use by the operator and safety for the patient.

Even though the customized display screens for the setup parameters, the monitoring parameters and the alarm limits parameters will normally accomplish all of the functionality required by an operator, all of the parameters associated with the dialysis machine are also available to be selected and the values associated with those parameters modified. The screen display presentation for all of the parameters, including those which are otherwise displayed on the customized display screens, are conveniently accessible through selection of the defaults button 186 shown in the screen display 150 in FIG. 15. When the operator touches the defaults button 186, as shown by step 280 in FIG. 16, the entire list of default parameters is presented in the main window 152 (FIG. 15) and at step 282 (FIG. 16).

Figure 15:
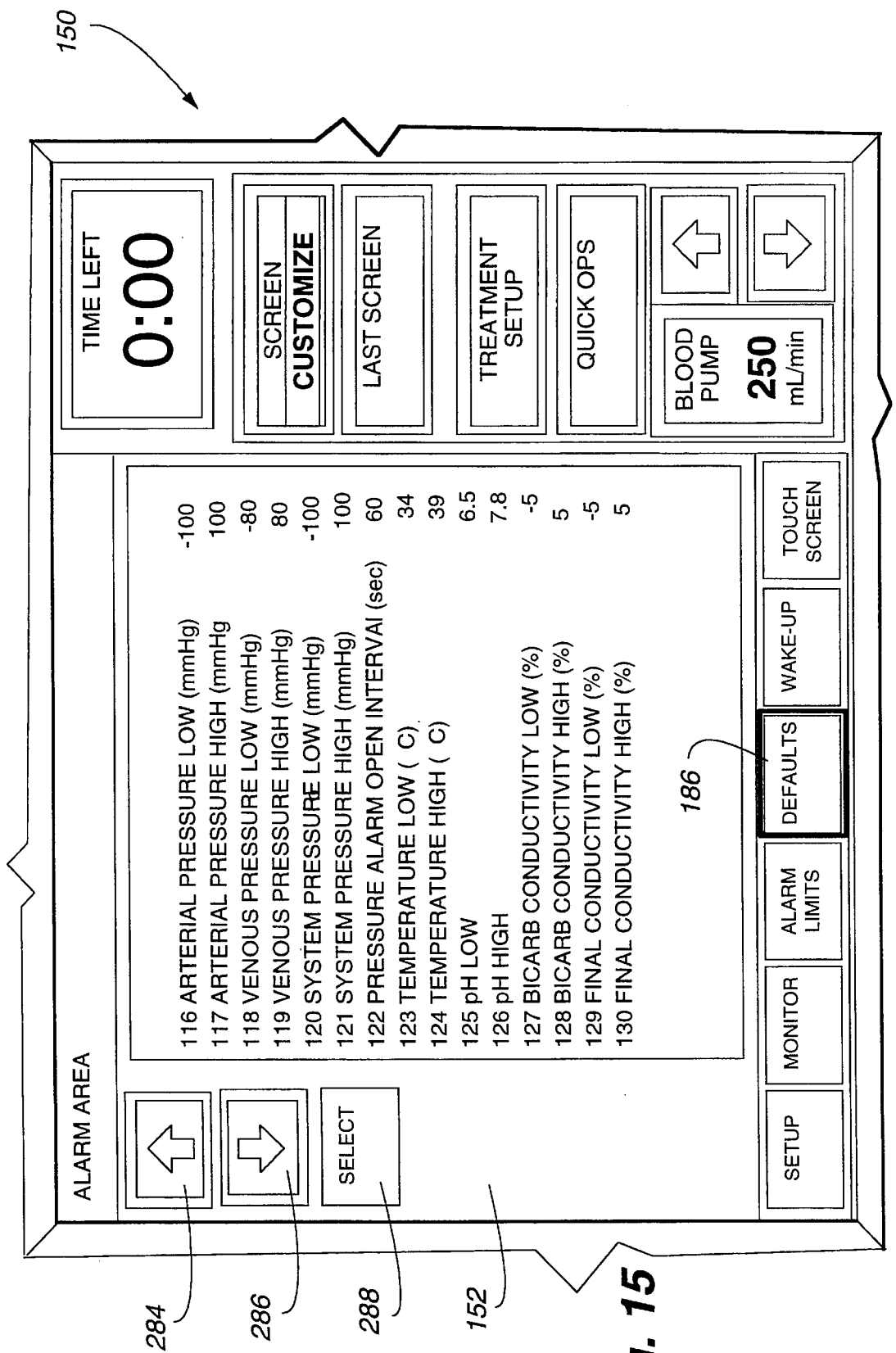
FIG. 15 is an illustration of a display screen of default parameters which may be selected for presentation in a default parameters display screen according to the present invention.
Figure 16:
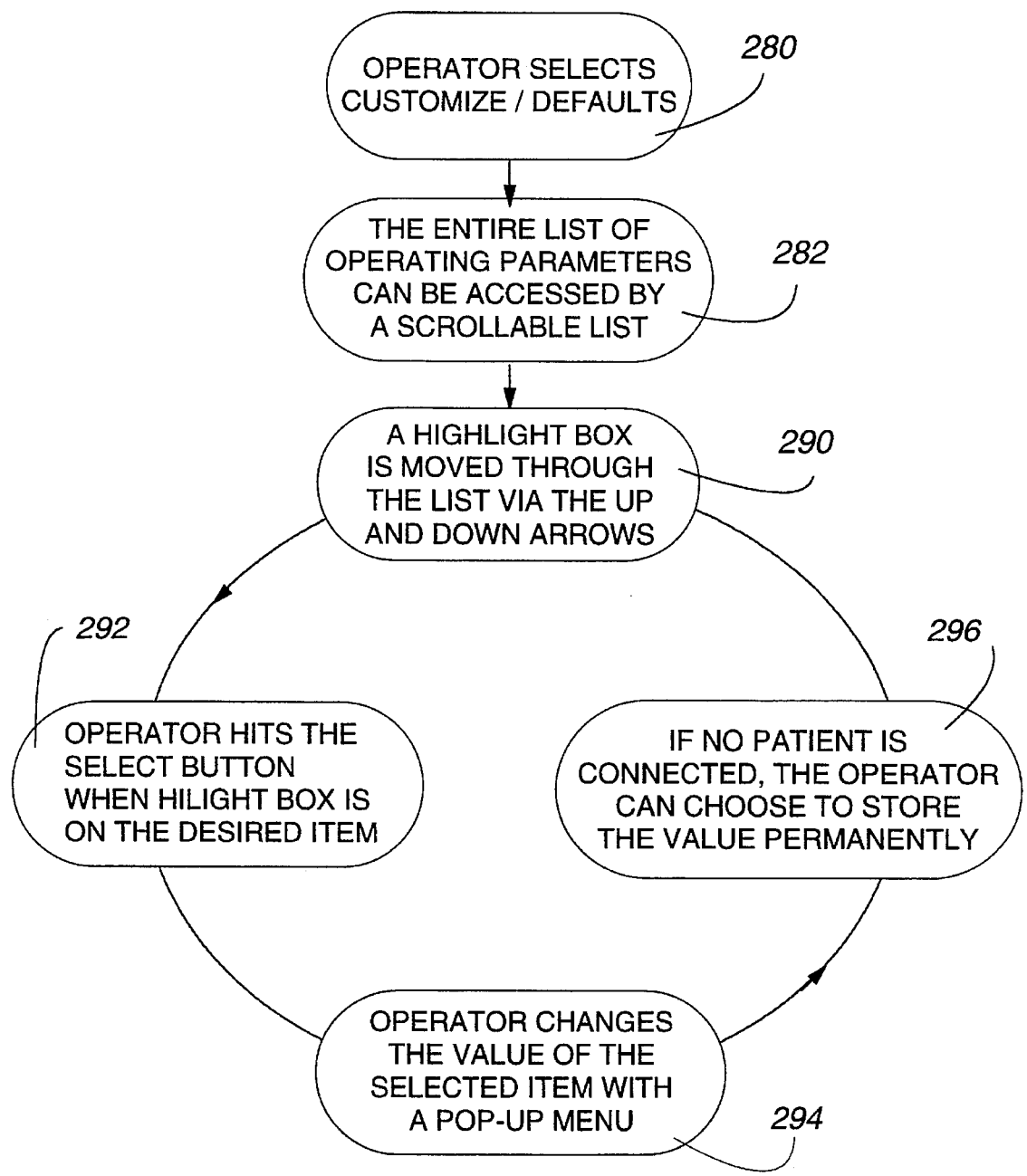
FIG. 16 is a flow chart of steps taken to select among the default parameters shown in FIG. 15 and to modify or establish values for the selected default parameters.

Also presented in the display screen shown in FIG. 15 is a scroll-up arrow 284 and a scroll-down arrow 286. Touching the arrows 284 and 286 causes a highlighted bar to move up and down the list of default parameters. Once the highlighted bar has been position over the selected default parameter, the operator touches a select button 288 to select the desired default parameter. Identifying the desired default parameter by use of the highlighted box and the scroll-up and scroll-down arrows is shown at step 290 (FIG. 16), and selecting that default parameter is shown at step 292. After the desired default parameter has been selected, the value of that parameter is available to be changed by use of the popup keypad 214 shown in FIG. 7. Changing the default parameter value is shown at step 234 (FIG. 16). If the dialysis machine is connected to a patient the changed value of the selected default parameter immediately takes effect. However if the machine is not connected to a patient as shown at step 296, the operator may store the changed value of the parameter to memory.

The defaults parameter display screen allows the operator to quickly and conveniently obtain access to every parameter available in the machine. Thus, any parameter which may not have been included in any of the options for customized display screens is available to be modified. Total flexibility in the use and programming of the dialysis machine is therefore available to the operator in a convenient and easy to use manner provided by the graphical display and programming capabilities of the defaults functionality.

Aspects of the present invention allow the machine operator to customize a schedule for an automatic cleaning and disinfecting function of the machine. This automatic functionality is discussed in detail in the concurrently filed application for a Technique for Automatically Preparing Dialysis Machine at a Predetermined Date and Time, Ser. No. 08/484,013. In general, this automatic functionality allows the hydraulics flow path other than the dialyzer to be completely cleaned and disinfected as a result of the machine automatically conducting the appropriate cleaning and disinfecting solutions through the machine, prior to the time when the machine will be used for dialysis treatments. The advantage of this automatic feature is that the time of the operator need not be devoted to the cleaning and disinfecting functions, but can be focused on the protective activity of dialysis treatments.

Figure 17:
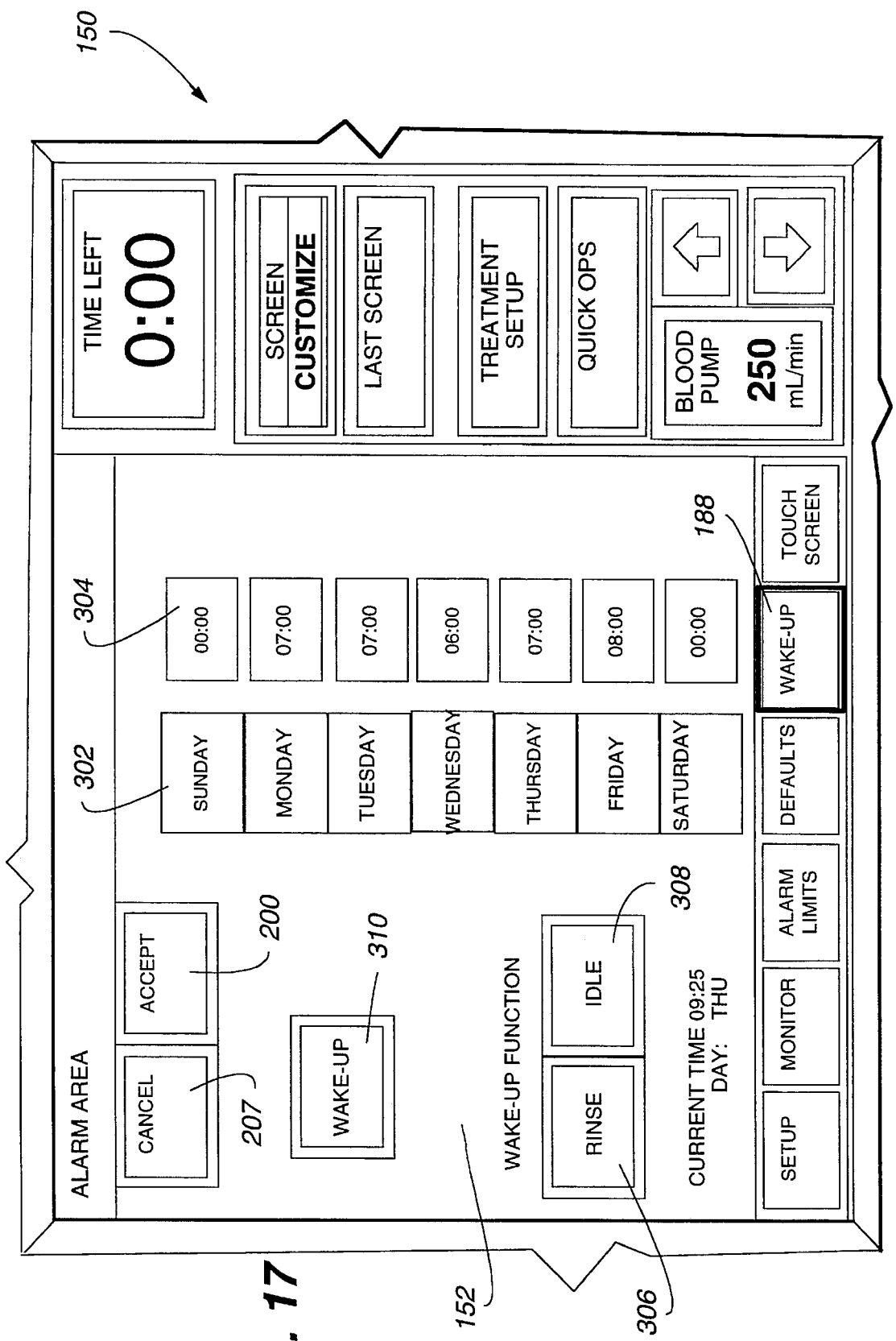
FIG. 17 is an illustration of a display screen of wake-up programming parameters which may be selected according to the present invention.

The ability to program the dialysis machine to start this automatic cleaning and disinfecting functionality at a particular time is one of the features of this invention. This programming capability is referred to as "wake-up" customization. Programming the wake-up times is achieved by touching the wake-up button 188 as shown in FIG. 17 to thereby accomplish the step 238 shown in FIG. 18. The main window 152 of the display screen 150 presents the operator with the buttons used to program the wake-up features, as shown at step 300 (FIG. 18).

The buttons presented to the operator include a button 302 identifying each day of the week when the operator desires to use the wake-up feature of the dialysis machine. Buttons 304 adjacent to the days of the week buttons 302 allow the operator to select the time of day to start the wake-up functionality. The wake-up functionality itself is selectable by the operator at buttons 306 and 308. A rinse button 306 is used to program a rinsing function. An idle button 308 is used to program an idle function which generally describes the state of the dialysis machine after the initial start and execution of all of the self-tests and other similar functions. Another wake-up button 310 is located in the main window area 152 to present the operator with the option of enabling or disabling the entire wake-up function. Although the rinse button 306 and idle button 308 are illustrated, any of the functions normally performed in preparation of a dialysis treatment could be programmed in a similar manner by adding more button displays.

Figure 18:
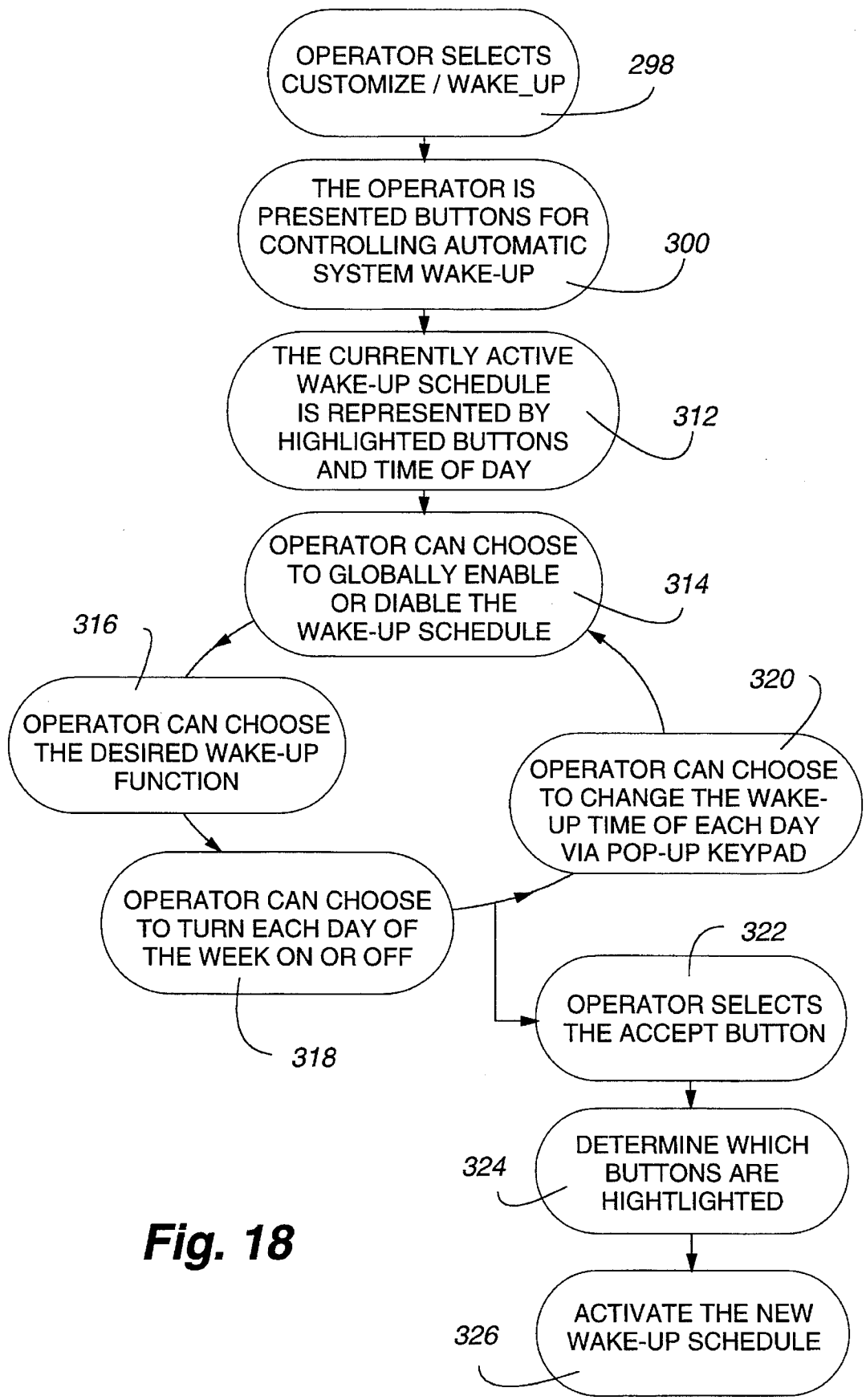
FIG. 18 is a flow chart of steps taken to select the wake-up parameters shown in FIG. 17 and to modify or establish values for the wake-up programming parameters.
Figure 19:
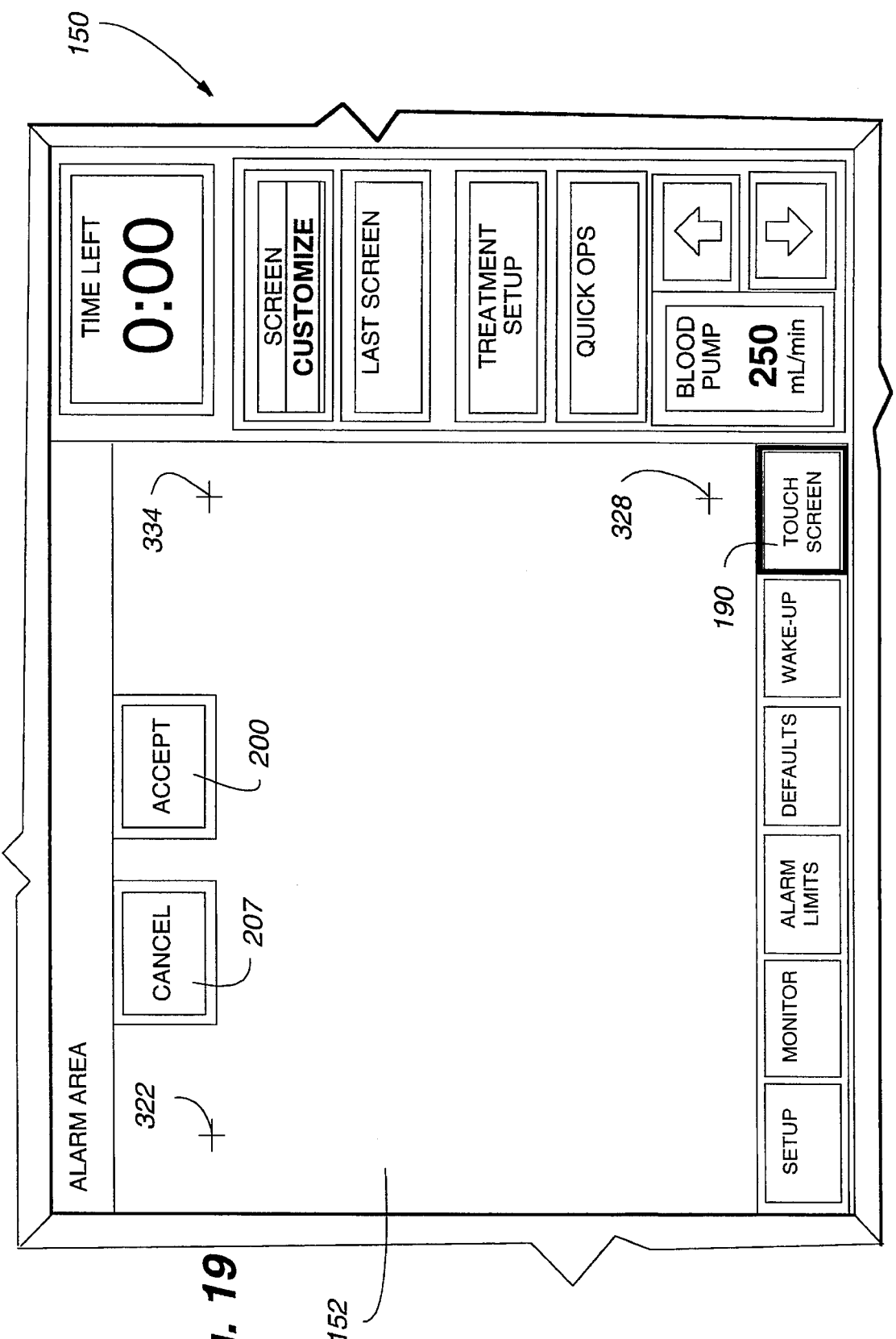
FIG. 19 is an illustration of a display screen of touch screen calibration parameters which may be selected according to the present invention.

Using the buttons presented in the display screen 150 shown in FIG. 17, the operator accomplishes the steps shown in FIG. 18. Once the buttons are displayed, the active features are shown by highlighted buttons, and the times and days when those functions become active are also highlighted as shown at step 312. The operator first makes the selection to enable or disable the wake-up function at step 314 by touching the wake-of button 310 (FIG. 18) to toggle between an enabled condition or a disabled condition. The operator chooses the desired wake-up function at step 316 by touching one of the buttons 306 or 308 (FIG. 17). Next the operator chooses the days of the week when the wake-up function is desired by touching those days of the week buttons 302 (FIG. 17) to highlight the days desired, as shown at step 318 (FIG. 18). By touching the times of the day buttons 304 (FIG. 17) to highlight the desired starting time, the popup keypad is presented to the operator. Using the keypad the operator enters the starting time as shown at step 320 (FIG. 18).

All of the days of the week are programmed with the desired wake-up function and the desired time by repeating the steps 314, 316, 318 and 320. Once all of this programming has been accomplished, the accept button 200 (FIG. 17) is touched to accept this programming at step 322 (FIG. 18). The OMI/protective microcontroller 122 determines which of the buttons have been highlighted at step 324 and establishes the new wake-up schedule at step 326 based on these selections.

One of the important requirements of the graphical touch screen programming employed in the present invention is an ability to accurately correlate the touch points on the screen to the desired selection presented to the operator. Correlation between the touch point and the displayed information is accomplished by the operator touching the touch screen button 190, shown in FIG. 19. The step of touching the touch screen button 190 is shown at 328 in FIG. 20.

Figure 20:
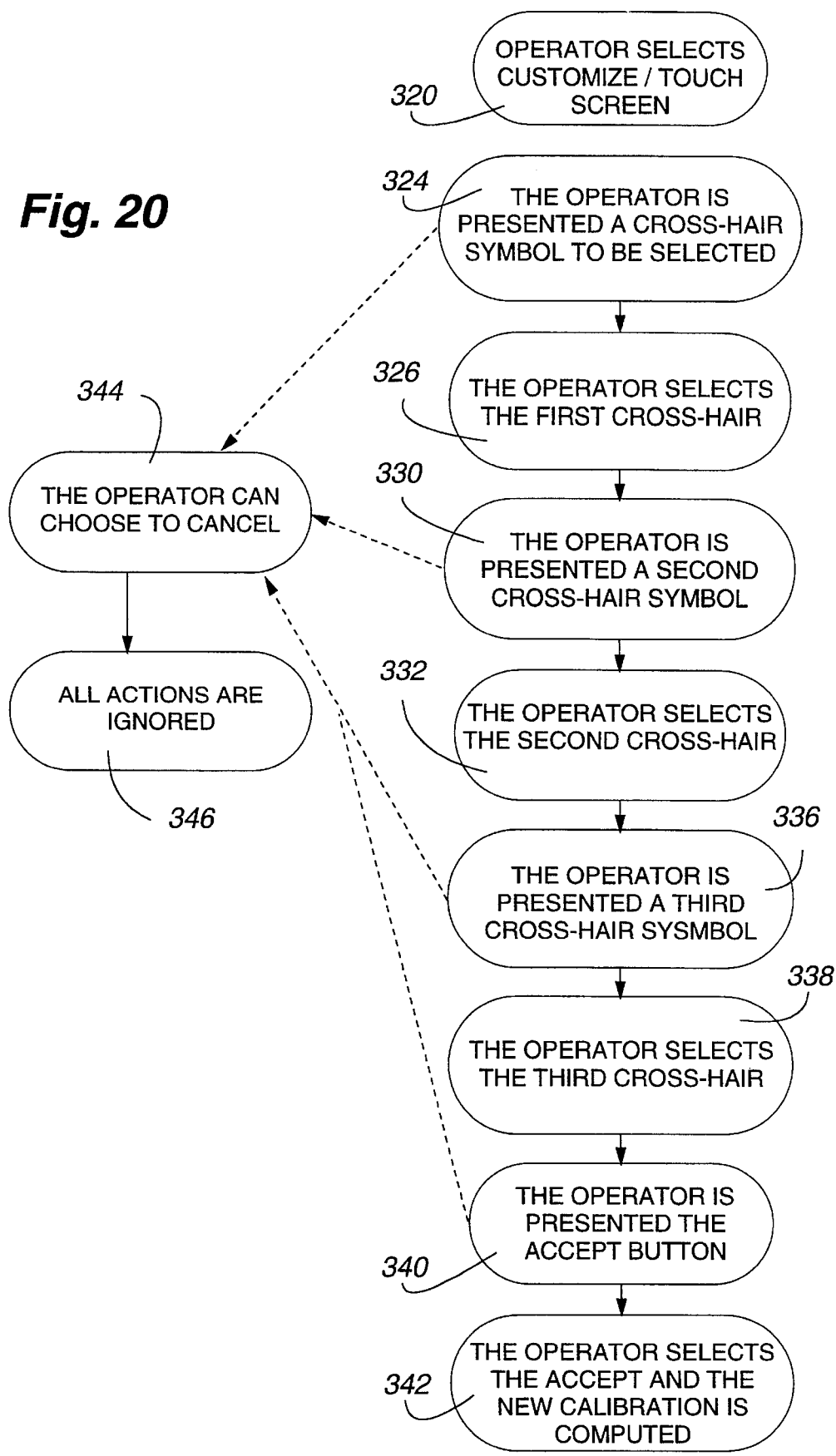
FIG. 20 is a flow chart of steps taken to select the calibration parameters shown in FIG. 19 and to establish those parameters withing in the dialysis machine shown in FIGS. 1 and 3.

As a result of selecting the touch screen button 190, a first cross-hair symbol 322 (FIG. 19) is displayed in the main window 152 at step 324 (FIG. 20). The operator touches the first cross-hair symbol at step 326. Thereafter a second cross-hair symbol 328 (FIG. 19) is displayed at step 330 (FIG. 20). Again the operator touches the second cross hair symbol at step 332 (FIG. 20). A third cross-hair symbol 334 (FIG. 19) is presented to the operator at step 336 (FIG. 20), and again the operator touches that symbol at step 338.

After all three cross-hair symbols have been presented and touched, the accept button 200 (FIG. 19) is presented to the operator at step 340 (FIG. 20). The operator touches the accept button at step 342 and the information is delivered to the OMI/protective microcontroller 122 (FIG. 3). This information correlates the location of the touch points to the location of the cross-hairs and thereby calibrates the location of the screen images to the touch points.

Of course, if the operator is not satisfied with any of the touch points relative to the cross-hairs, the cancel button 207 (FIG. 19) can be touched at any time during the procedure shown in FIG. 20, as represented by step 344. The effect of touching the cancel button at step 344 is to cause all of the previous information obtained from the touch screen procedure shown in FIG. 20 to be disregarded as shown at step 346.

The graphical OMI of the present invention offers significant convenience and flexibility in allowing the operator to access most of the important parameters associated with safely operating a dialysis machine. Accessing these parameters allows the dialysis machine to be customized for optimal patient treatment and optimal operator efficiency during treatments. Optimal treatment is particularly important because of the increased emphasis on varying some of the operating and monitoring parameters which traditionally have not been varied or available to be varied, particularly by the operator of the machine. As a result, the present invention represents a significant advancement in the flexibility and adaptability of dialysis machines for optimal patient treatment and clinical use.

A presently preferred embodiment of the invention and many of its improvements have been described with a degree of particularity. This description is a preferred example for implementing the invention, and is not necessarily intended to limit the scope of the invention which is defined by the following claims.

The invention claimed is:

1. A dialysis machine having a graphical operator machine interface ("OMI") by which to establish machine operating and dialysis treatment parameters employed by the dialysis machine in a dialysis treatment, wherein the graphical OMI comprises:

a graphical screen by which to access, select, display and enter information;

means accessible through the graphical screen for displaying on the graphical screen in a first screen display a first predetermined group of a plurality of predetermined machine operating and dialysis treatment parameters used by the dialysis machine in a dialysis treatment;

means accessible through the graphical screen for entering parameter selection information at the first screen display to select a second selected group of the parameters from the first group, the second selected group formed by a lesser number of the parameters than are present in the first group; and means responsive to the parameter selection information entered at the first screen display for displaying the second selected group of parameters on the graphical screen in a second screen display, the second screen display being different from the first screen display.

2. A dialysis machine as defined in claim 1 wherein the graphical OMI further comprises:

means accessible through the graphical screen for entering parameter selection information at the second screen display to select a third selected group of the parameters from the second selected group;

means responsive to the selection information of the third selected group of parameters entered at the second screen display for displaying a value entry display screen on the graphical screen in conjunction with the second screen display; and means accessible through the value entry display screen for entering information establishing values for each of the parameters of the third selected group.

3. A dialysis machine as defined in claim 2 wherein the graphical OMI further comprises:

means accessible through the value entry display screen for entering acceptance information at the value entry display screen to accept the values established for each of the parameters of the third selected group.

4. A dialysis machine as defined in claim 3 wherein the graphical OMI further comprises:

means responsive to the acceptance information entered at the value entry display screen for displaying the established values accepted for each parameter of the second selected group displayed in the second display screen.

5. A dialysis machine as defined in claim 4 wherein the graphical OMI further comprises:

means responsive to the acceptance information entered at the value entry display screen for all of the established values for the third selected group of parameters to remove the value entry display screen from the second display screen.

6. A dialysis machine as defined in claim 4 wherein the parameters of the third selected group are setup parameters for operating the dialysis machine.

7. A dialysis machine as defined in claim 4 wherein the parameters of the third selected group are monitoring parameters for monitoring the operation of the dialysis machine.

8. A dialysis machine as defined in claim 4 wherein the parameters of the third selected group are alarm limits parameters for establishing operational limits for the dialysis machine.

9. A dialysis machine as defined in claim 4 wherein the parameters of the third selected group are time parameters for initiating the operation of the dialysis machine at a predetermined time prior to use of the machine for treatment.

10. A dialysis machine as defined in claim 9 wherein the parameters of the third selected group are parameters establishing a cleaning operation for at least a part of a hydraulics flow path within the dialysis machine.

11. A dialysis machine as defined in claim 9 wherein the parameters of the third selected group establish a priming operation for at lease a part of a hydraulics flow path in an extracorporeal flow path within the dialysis machine.

12. A dialysis machine as defined in claim 4 wherein the parameters of the third selected group are parameters for programming the operation of the dialysis machine for treatment.

13. A dialysis machine as defined in claim 1 wherein the parameters of the first predetermined group are substantially all parameters necessary for operating the machine and performing dialysis treatment.

14. A method of programming a dialysis machine using a graphical operator machine interface to establish machine operating and dialysis treatment parameters employed by the dialysis machine in a dialysis treatment, comprising the steps of:

using a graphical screen to access, select, display and enter information;

displaying in a first screen display on the graphical screen a first predetermined group of a plurality of predetermined machine operating and dialysis treatment parameters used by the dialysis machine in a dialysis treatment; and entering parameter selection information on the graphical screen at the first screen display to select a second selected group of the parameters from the first group, the second selected group formed by a lesser number of the parameters than are present in the first group; and thereafter displaying the second selected group of parameters on the graphical screen in a second screen display, the second screen display being different from the first screen display.

15. A method as defined in claim 14 further comprising the steps of:

entering parameter selection information at the second screen display to select a third selected group of parameters from the second selected group;

displaying a value entry display screen on the graphical screen in conjunction with the second screen display after entering the parameter selection information to select the third selected group of parameters; and entering information establishing values for each of the parameters of the third selected group by accessing the value entry display screen.

16. A method as defined in claim 15 further comprising the step of:

entering acceptance information at the value entry display screen to accept the values established for each of the parameters of third group.

17. A method as defined in claim 16 further comprising the step of:

removing the value entry display screen after entering all of the values for each parameter of the third selected group of parameters.

18. A method as defined in claim 16 further comprising the step of:

displaying on the second display screen the values accepted for each parameter of the second selected group after the acceptance information has been entered.

19. A method as defined in claim 18 wherein the parameters of the third selected group are setup parameters for operating the dialysis machine.

20. A method as defined in claim 18 wherein the parameters of the third selected group are monitoring parameters for monitoring the operation of the dialysis machine.

21. A method as defined in claim 18 wherein the parameters of the third selected group are alarm limits parameters for establishing operational limits for the dialysis machine.

22. A method as defined in claim 18 wherein the parameters of the third selected group are time parameters for initiating a cleaning and disinfecting operation at a predetermined time prior to use of the machine for treatment, the cleaning and disinfecting operation occurring within at least a part of a hydraulics flow path of the dialysis machine.

23. A method as defined in claim 18 wherein the parameters of the third selected group establish a priming operation for at least a part of a hydraulics flow path in an extracorporeal flow path of the dialysis machine.

24. A method as defined in claim 18 wherein the parameters program the operation of the dialysis machine for treatment.

25. A method as defined in claim 18 wherein the parameters of the first predetermined group are substantially all of those parameters for operating the machine and performing dialysis treatment.

26. A dialysis machine having a graphical operator machine interface ("OMI") by which to establish machine operating and dialysis treatment parameters employed by the dialysis machine in a dialysis treatment, wherein the graphical OMI comprises:

a graphical screen by which to access, select, display and enter information;

a screen display circuit connected to the graphical screen to display on the graphical screen a plurality of screen displays, the plurality of screen displays include a first screen display of a first predetermined group of a plurality of predetermined machine operating and dialysis treatment parameters; and a touch-responsive input circuit connected to the graphical screen and to the screen display circuit, each screen display on the graphical screen being correlated with the input circuit to allow touch-responsive entering of information correlated to the screen display;

the input circuit responding to entered information from the first display screen to identify a plurality of parameters from the first predetermined group and to assemble the identified parameters from the first predetermined group into a second selected group formed of a lesser number of the parameters than are present in the first predetermined group; and the screen display circuit responding to the identification of the second selected group of parameters to display the second selected group of parameters on the graphical screen in a second screen display, the second screen display being different from the first screen display.

27. A dialysis machine as defined in claim 26 wherein:

the input circuit is responsive to selection information entered at the second screen display to identify a third selected group of parameters selected from the second group;

the display circuit is responsive to the third selected group of parameters to display a value entry display screen in conjunction with the second screen display; and the input circuit is responsive to information entered through the value entry display screen to establish values for each of the parameters of the third selected group.

28. A dialysis machine as defined in claim 27 wherein:

the input circuit is responsive to acceptance information entered at the value entry display screen to accept the values established for each of the parameters of the third group.

29. A dialysis machine as defined in claim 28 wherein:

the input circuit is responsive to the acceptance information for all of the established values of the third selected group of parameters thereafter to remove the value entry display screen from the second screen display.

30. A dialysis machine as defined in claim 28 wherein:

the display circuit is responsive to the acceptance information entered at the value entry display screen to display the accepted values in association with each parameter of the second selected group presented in the second display screen.

31. A dialysis machine as defined in claim 27 wherein the parameters of the third selected group are setup parameters for operating the dialysis machine.

32. A dialysis machine as defined in claim 27 wherein the parameters of the third selected group are monitoring parameters for monitoring the operation of the dialysis machine.

33. A dialysis machine as defined in claim 27 wherein the parameters of the third selected group are alarm limits parameters for establishing operational limits for the dialysis machine.

34. A dialysis machine as defined in claim 27 wherein the parameters of the third selected group are time parameters for initiating the operation of the dialysis machine at a predetermined time prior to use of the machine for treatment.

35. A dialysis machine as defined in claim 34 wherein the parameters of the third selected group include parameters establishing a cleaning operation for at least a part of a hydraulics flow path within the dialysis machine.

36. A dialysis machine as defined in claim 34 wherein the parameters of the third selected group include parameters establishing a priming operation for at least a part of a hydraulics flow path and an extracorporeal flow path within the dialysis machine.

37. A dialysis machine as defined in claim 27 wherein the parameters of the third selected group are parameters for programing the operation of the dialysis machine for treatment.

38. A dialysis machine as defined in claim 27 wherein the parameters of the first predetermined group are substantially all of those parameters necessary for operating the machine and performing dialysis treatment.

* * * * *